United States Patent
Wagner

(10) Patent No.: US 12,178,732 B2
(45) Date of Patent: *Dec. 31, 2024

(54) SYSTEMS AND DEVICES FOR PROVIDING LIFT ASSISTANCE FOR A SURGICAL PROCEDURE

(71) Applicant: Mizuho Orthopedic Systems, Inc., Union City, CA (US)

(72) Inventor: Peter E. Wagner, Danville, CA (US)

(73) Assignee: Mizuho Orthopedic Systems, Inc., Union City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,359

(22) Filed: May 22, 2023

(65) Prior Publication Data

US 2023/0293331 A1 Sep. 21, 2023

Related U.S. Application Data

(63) Continuation of application No. 16/817,053, filed on Mar. 12, 2020, now Pat. No. 11,690,749.

(60) Provisional application No. 62/817,483, filed on Mar. 12, 2019.

(51) Int. Cl.
*A61F 5/04* (2006.01)
*A61F 5/01* (2006.01)
*A61G 13/12* (2006.01)

(52) U.S. Cl.
CPC .......... *A61F 5/0193* (2013.01); *A61G 13/123* (2013.01); *A61G 13/1245* (2013.01)

(58) Field of Classification Search
CPC .. A61F 5/048; A61F 5/042; A61F 5/04; A61F 5/0193; A61G 13/123; A61G 13/1245; A61G 13/08; E05D 3/14; E05D 3/12; F16C 11/0661; F16C 11/0695; Y10T 403/32032

See application file for complete search history.

(56) References Cited

U.S. PATENT DOCUMENTS

| | | |
|---|---|---|
| 5,056,535 A | 10/1991 | Bonnell |
| 6,108,841 A | 8/2000 | Cameron et al. |
| 6,704,959 B2 | 3/2004 | Schuerch |
| 7,243,654 B2 | 7/2007 | Schuerch |
| 7,951,097 B2 * | 5/2011 | Schaeffer ............. A61H 1/0281 601/24 |
| 9,119,610 B2 | 9/2015 | Matta et al. |
| 10,188,573 B2 | 1/2019 | Moriarty et al. |

(Continued)

FOREIGN PATENT DOCUMENTS

| | | |
|---|---|---|
| DE | 202016101587 U1 | 8/2016 |
| EP | 2873404 A1 | 5/2015 |

OTHER PUBLICATIONS

International Search Report and Written Opinion for PCT/US20/22372.

(Continued)

*Primary Examiner* — Camtu T Nguyen
(74) *Attorney, Agent, or Firm* — Reed Smith LLP; Matthew P. Frederick; Anupma Sahay

(57) ABSTRACT

Systems and devices oriented in a compact manner provide lift assistance to a spar of a surgery table for hip, leg-related surgeries, or generally lower limb related orthopedic procedures. The compact device does not impede the radiolucency of the spar below the patient's hip, trochanter, or femur.

20 Claims, 21 Drawing Sheets

(56) References Cited

U.S. PATENT DOCUMENTS

| | | |
|---|---|---|
| 10,206,842 B2 | 2/2019 | Labedz et al. |
| 10,869,801 B1 | 12/2020 | Skripps et al. |
| 11,077,006 B2 | 8/2021 | Labedz et al. |
| 2005/0160533 A1* | 7/2005 | Boucher ................ A61G 13/12 5/624 |
| 2011/0023893 A1 | 2/2011 | Striggow et al. |
| 2013/0192609 A1 | 8/2013 | Bellows |
| 2014/0243716 A1* | 8/2014 | Diot ....................... A61G 7/075 601/5 |
| 2016/0120726 A1 | 5/2016 | Moriarty et al. |
| 2019/0358110 A1 | 11/2019 | Schuerch, Jr. |

OTHER PUBLICATIONS

Extended European Search Report dated Nov. 2, 2022 for EP 20769838.2.

* cited by examiner

SYSTEMS AND DEVICES FOR PROVIDING LIFT ASSISTANCE FOR A SURGICAL PROCEDURE

PRIORITY

This application is a continuation of U.S. patent application Ser. No. 16/817,053 of the same title filed Mar. 12, 2020 and claims the benefit of priority to U.S. Patent Application Ser. No. 62/817,483 of the same title filed Mar. 12, 2019, under U.S.C. § 119, the entire contents of each which are incorporated herein by reference.

BACKGROUND

Technological Field

The present application relates generally to systems and devices used in surgical procedure, and more specifically to systems and devices for providing lift assistance for hip-related surgeries or lower limb orthopedic procedures.

SUMMARY

The invention relates to systems and devices that do not impede the radiolucency of a spar or an articulating limb support below the patient's hip, trochanter, or femur, and provide lift assistance to such spar or the articulating limb support.

Exemplary embodiments described herein have innovative features, no single one of which is indispensable or solely responsible for their desirable attributes. Without limiting the scope of the claims, some of the advantageous features will now be summarized.

The inventive concepts disclosed herein offer superior control and access to the operative site that provide assisted movement of the anatomy for numerous orthopedic surgical procedures, for example, including but not limited to Anterior Approach Total Hip Arthroplasty (AATHA), fracture reduction, hip fracture; tibial fracture; acetabular & pelvic fracture; femur fracture; thoracic & lumbar spine; hip arthroscopy & resurfacing. The systems and device provide improved imaging area with unobstructed views and facilitate positioning requirements for a range of patients, while providing intuitive and ergonomic controls that are designed for both patient and staff safety that aid in simple and assisted articulation.

The systems and devices disclosed herein are oriented in a compact manner such that components are distal to the spar, which is proximal to the patient's hip. One skilled in the art may appreciate that reference to spar herein may equivalently be referred to, or correspond to, for instance, an articulating limb support or an articulating lower limb support. Such compact design does not impede the radiolucency of the spar below the patient's hip, trochanter, or femur. Additionally, the compact design includes a swing arm that further aids in articulation of the spar and the accompanying limb.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a," "an," and "the" include plural referents unless the context clearly dictates otherwise.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

Figure 1A:
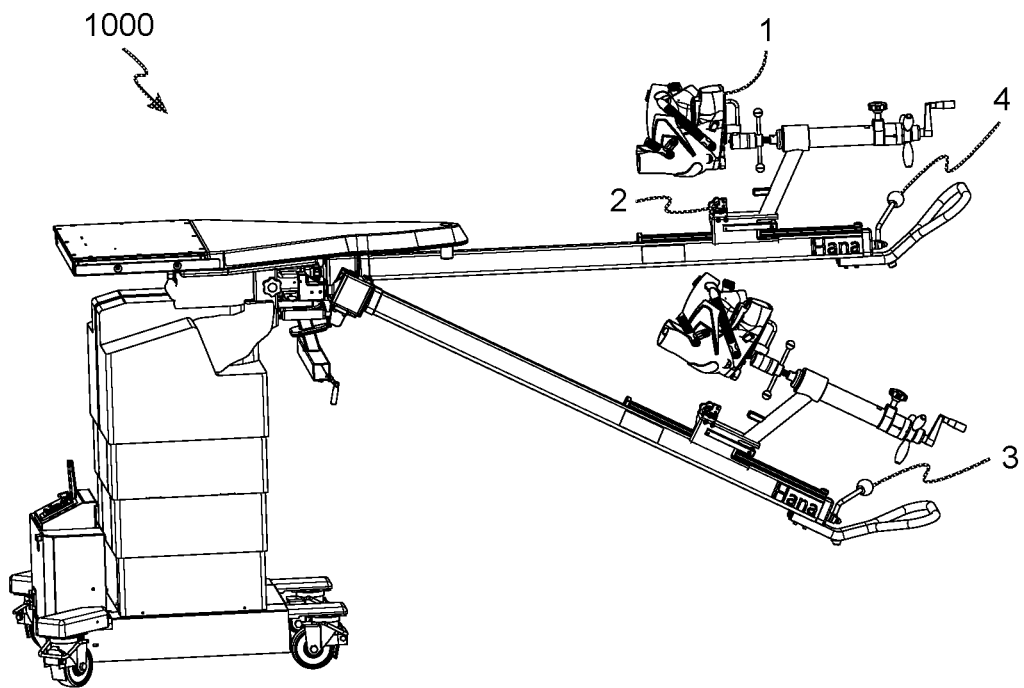
FIG. 1A is a side view of the system including a surgery table and leg support spar device in accordance with some embodiments of this disclosure.

Various aspects of the novel systems, apparatuses, and methods disclosed herein are described more fully hereinafter with reference to the accompanying drawings. This disclosure can, however, be embodied in many different forms and should not be construed as limited to any specific structure or function presented throughout this disclosure. Rather, these aspects are provided so that this disclosure will be thorough and will fully convey the scope of the disclosure to those skilled in the art. Based on the teachings herein, one skilled in the art would appreciate that the scope of the disclosure is intended to cover any aspect of the novel systems, apparatuses, and methods disclosed herein, whether implemented independently of, or combined with, any other aspect of the disclosure. For example, an apparatus may be implemented or a method may be practiced using any number of the aspects set forth herein. In addition, the scope of the disclosure is intended to cover such an apparatus or method that is practiced using other structure, functionality, or structure and functionality in addition to or other than the various aspects of the disclosure set forth herein. It should be understood that any aspect disclosed herein may be implemented by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, and/or objectives. The detailed description and drawings are merely illustrative of the disclosure rather than limiting, the scope of the disclosure being defined by the appended claims and equivalents thereof.

It will be recognized that while certain aspects of the disclosure are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the disclosure disclosed and claimed herein.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments and/or implementations may be understood and effected by those skilled in the art in practicing the claimed disclosure, from a study of the drawings, the disclosure and the appended claims.

Figure 1B:
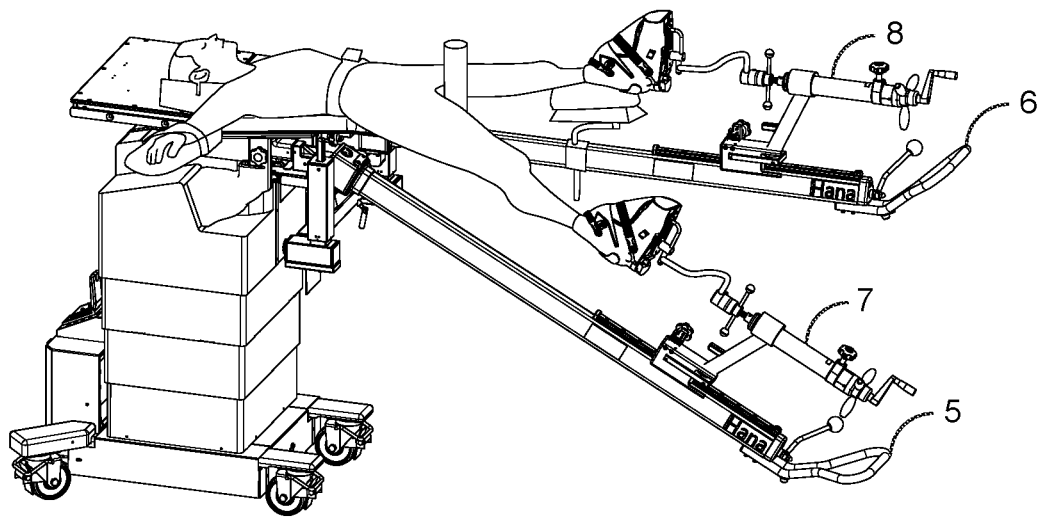
FIG. 1B is a side view of a patient on the surgery table illustrated in FIG. 1A with a limb of the patient coupled to the leg support spar device for performing surgical procedure on the patient.

FIGS. 1A-1B illustrate an embodiment of a system including a surgery table with at least one spar coupled thereto. One skilled in the art may appreciate that reference to spar herein may equivalently be referred to, or correspond to, for instance, an articulating limb support or an articulating lower limb support. As illustrated, in FIG. 1B, a patient undergoing a particular surgery will have his or her leg positioned in a traction boot 1, 2 that is coupled to a respective spar. Further, as illustrated in FIGS. 1A-1B, the system includes brake handles 3, 4; user grips 5, 6; and articulation joints 7, 8 that are coupled to the respective spar. As illustrated, at least two spars extending from the surgery table are shown, wherein each respective spar includes its own respective brake handle, user grip and articulation joint. The open boot design provides sustained traction during the procedure for a range of foot sizes. A conveniently located ratchet provides quick, secure positioning with additional heel strap support. The quick release ratchets enable easy removal of the patient's foot from the traction boot 1, 2, and a screw lock makes the traction boot 1, 2 easy to attach and remove from the traction device, thereby providing a system that provides simple articulation. This system enables one person to have control of the slide, traction and rotation of the traction boot 1, 2 with one hand and fluid movement of the leg spar with the other. It allows for complete focus on the patient, and a full range of motion without interference from the equipment. The articulation joints 7, 8 may be tubular structures that provide fine traction and rotation to the traction boot 1, 2 about the patient's tibia.

The systems and devices illustrated in FIGS. 1A-1B provide almost limitless positioning options, to create the optimum vantage point for surgeons, all with the confidence of two hands. The systems and devices include safety locks that engage in order to prevent and avoid uncontrolled or unintended movements as the spar brake handles 3, 4 are engaged. Stated differently, the user may engage or actuate the brake handles 3, 4 to lock a respective spar 111 in position with respect to the surgery table. Likewise, the rotation axis may be unlocked to rotate, and thereafter relocked via a knob, which is on top side of the traction joints 7, 8. In certain embodiments, the fine traction automatically locks in place as the user adjusts it by rotating a non-back drivable lead screw using the handle at the extreme distal end of the traction assembly. One skilled in the art will appreciate that actuation of brake handles 3, 4 to lock spar in position may be either done manually or automatically.

Figure 2:
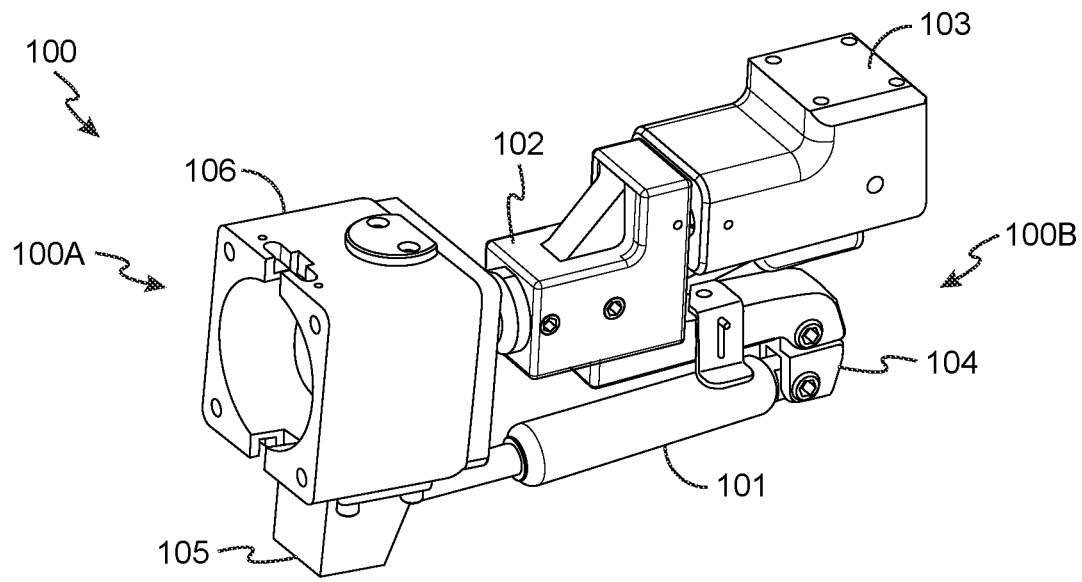
FIG. 2 is a perspective view of a lift assistance device employed with a surgery table as illustrated in FIG. 1A for providing lift assistance to a spar supporting a patient's limb during a surgical procedure.
Figure 3:
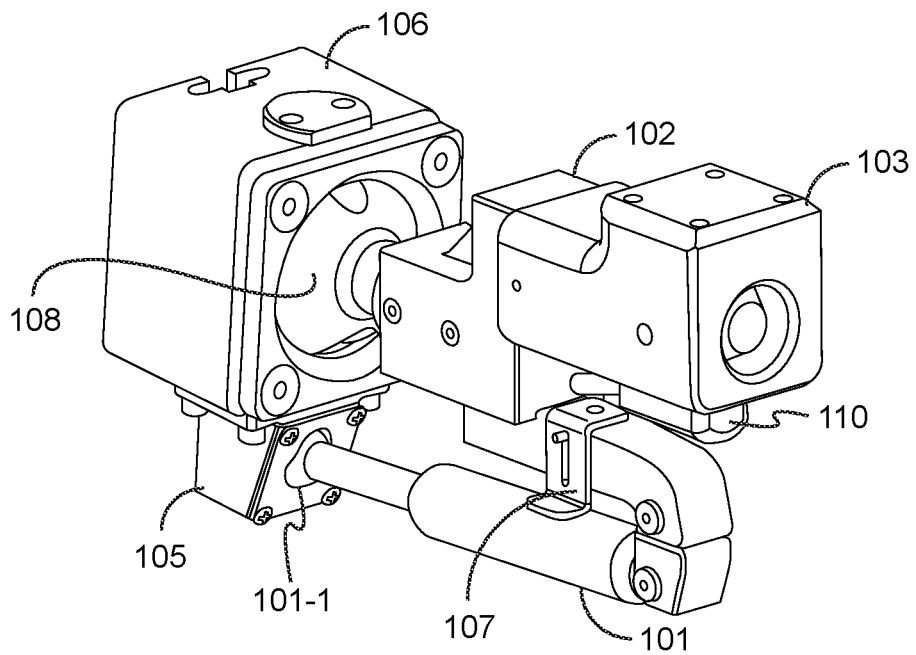
FIG. 3 is another perspective view of the lift assistance device coupled to a spar mount assembly, as shown in FIG. 2.
Figure 4:
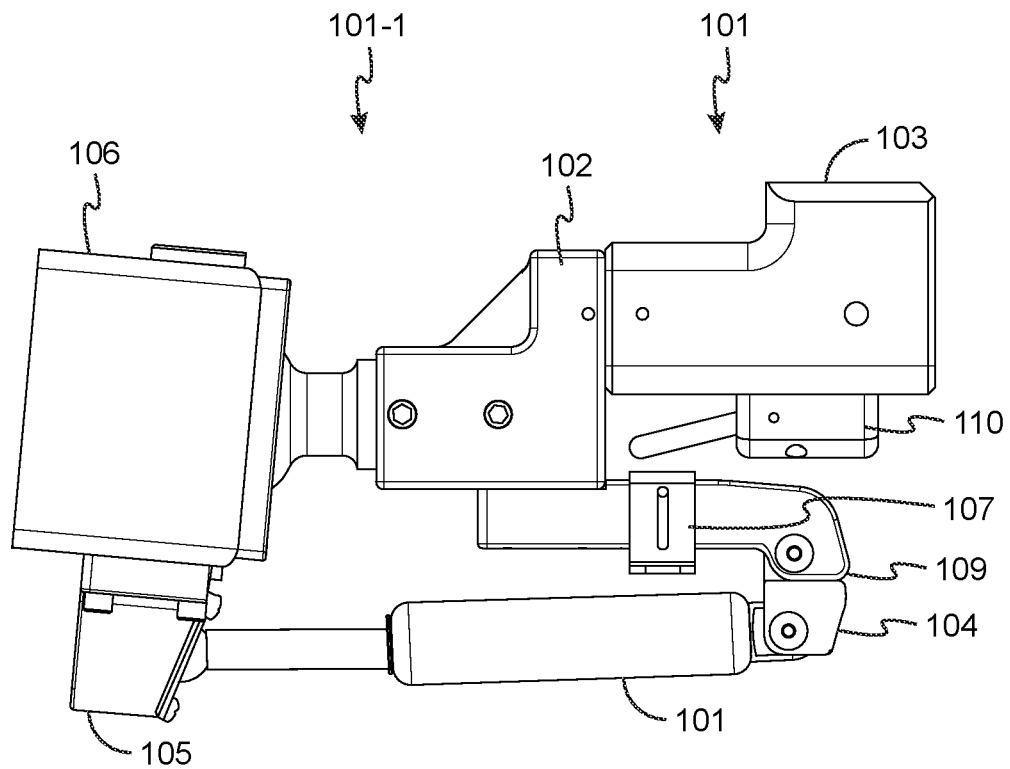
FIG. 4 is another perspective view of the lift assistance device coupled to the spar mount assembly, as shown in FIG. 2.

Next, referring to FIGS. 2-4, an embodiment of a lift assistance device 100 is discussed in detail. The lift assistance device 100 may be used with the system 1000 illustrated in FIGS. 1A-1B above such that the lift assistance device 100 may be employed with the surgery table and the spars shown in FIGS. 1A-1B. The lift assistance device 100 provides assisted movement to a user or an operating technician as he/she lifts the spar 111 with or without the limb of the patient attached thereto. FIG. 2 illustrates a perspective view of the device 100 that may be employed with a surgery table illustrated in FIG. 1A for purposes of providing lift assistance to a spar supporting a patient's limb during a surgical procedure. The device 100 includes a spring device 101, a swing arm 104, a joint mount 102, a joint housing 106, and a mount connector 112 (shown in FIG. 5A) that engages or is received within an opening or cavity in a spar mount assembly 103.

One skilled in the art would appreciate that spring device 101 may be a flexible, elastic device, or alternatively a rigid device that may include reciprocating pumps, gas or air compressors and pneumatic cylinders, magnetic pumps, tension/extension spring, compression spring, torsional spring, wire/coil spring, flat spring, among other similar mechanisms. The spring device 101 may transfer force from expending gas or air in cylinder via a piston rod; connecting rod; helical, spring, coiled, non-coiled, or flat springs, or other cylindrically shaped devices such that stored mechanical energy may be transferred between components. Alternatively, the spring device 101 may include hydraulics mechanism that operates through the force of liquid pressure such that via the hydraulics mechanism, mechanical movement is produced by contained, pumped liquid, through cylinders moving pistons.

Figure 5A:
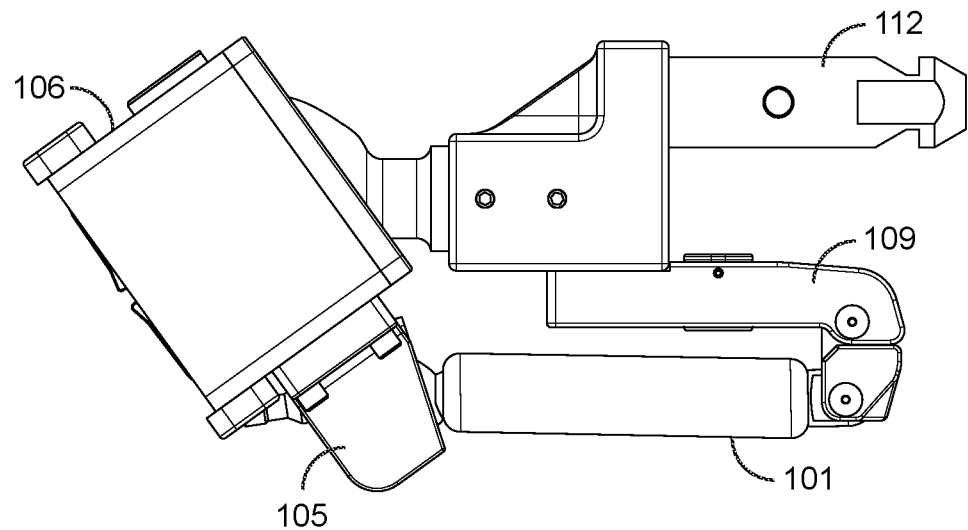
FIGS. 5A-5C are different actuation positions of the lift assistance device without being coupled to the spar mount assembly according to an example embodiment.
Figure 5B:
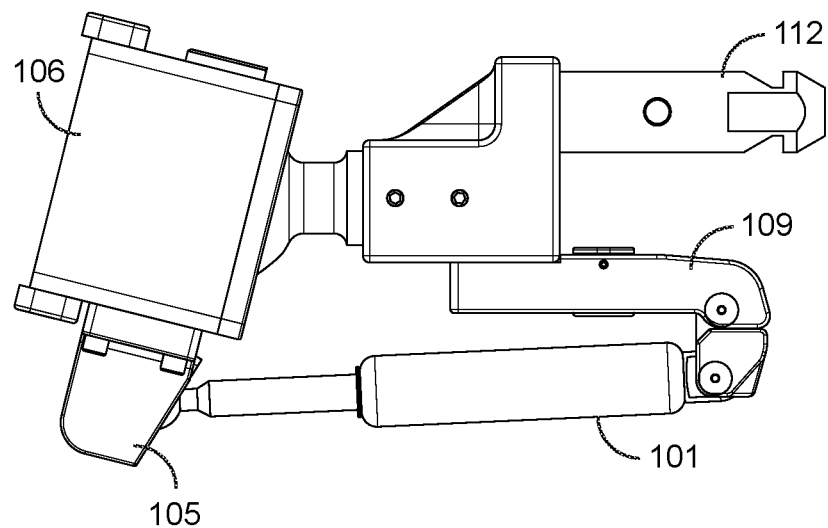
Figure 5C:
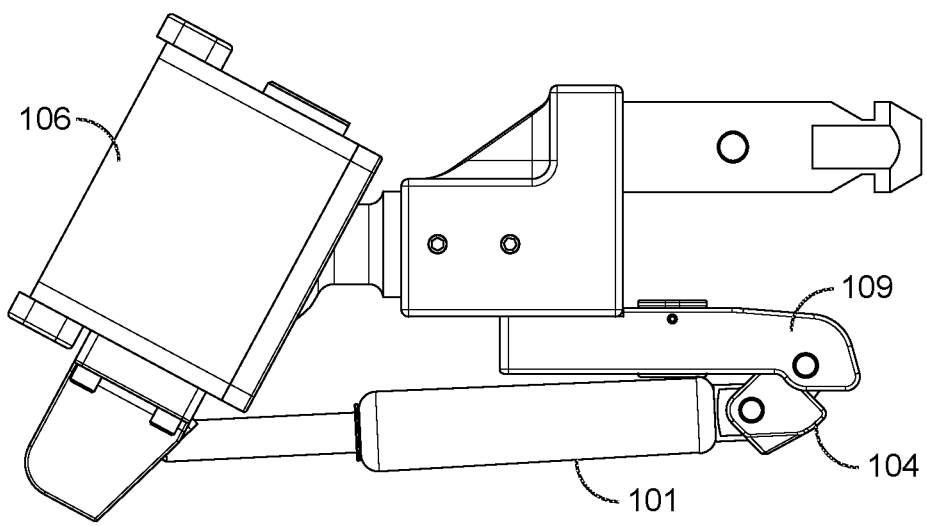

In certain embodiments, the spring device 101 is preloaded with at least 450 pounds (lbs) of force when in the extended position (illustrated in FIGS. 5B-C). In other embodiments, the spring device 101 may be preloaded with a force between 450 and 685 pounds (lbs) as it transitions between fully extended to fully compressed positions. As the spring device 101 is compressed the force increases by at least 1.52 times, to a max of 685 lbs. In still other embodiments, the spring device 101 may be preloaded with a force between 250 and 800 pounds (lbs). By nature of the spring device 101 providing force, the spring device 101 reduces the effort needed to lift a spar 111 supporting a patient's leg by at least 50%. In other embodiments, the spring device 101 reduces the effort needed to lift a spar 111 supporting a patient's leg in a range of from 43% to 72%. In still further embodiments, the spring device 101 reduces the effort needed to lift a spar 111 supporting a patient's leg in a range of from 20% to over 100%.

Still referring to FIGS. 2 and 3, the first joint illustrated by the joint housing 106 and ball member 108 and the second joint illustrated by ball member 101-1 and spring joint housing 105 are shown as ball and socket joints. For example, the joint housing 106 comprises a cavity, illustrated in FIGS. 2-3, wherein the cavity is configured to receive a ball member 108 that is extending from the joint mount 102. One skilled in the art may appreciate that the second joint coupling the spring device 101 and the joint housing 106 includes the same degree of freedom as the first joint and/or spar 111. However, the first joint and the second joint may be other types of joints as well, including planar joint, hinge joint, pivot joint, condyloid joint, saddle joint or ball-and-sock joint. The joints may include combinations of any of the aforementioned joints in order to achieve one or two or more degrees of freedom.

In certain embodiments, the device 100 includes a proximal end 100A and a distal end 100B (with respect to the spar 111). As illustrated in FIG. 2, the joint housing 106 is on the proximal end 100A of the device 100 (connects to the spar 111) and the joint mount 102 is on the distal end 100B of the device 100. The joint mount 102 further includes a mount connector 112 (illustrated in FIGS. 5A-5C) distally extending away from the joint mount 102. The joint mount 102 is coupled to the joint housing 106 comprising a first joint. In addition to these features, the device 100 includes spring device 101 that is positioned below and extends from the joint mount 102 to the joint housing 106. That is, the spring device 101 extends from about the proximal end 100A of the device 100 to the distal end 100B of the device 100.

In one embodiment, the mount connector 112 being configured to couple with a spar mount assembly 103, and maintain alignment of the joint mount 102 and the spring device 101 with the spar mount assembly 103 while the joint housing 106 transitions between the first and second positions, and as the spar 111 moves in at least two degrees of freedom.

The spring device 101 having a first end and a second end. The first end of the spring device 101 connected to the joint housing 106 by a second joint, comprised of the spring joint housing 105 and the ball member 101-1. And, wherein the second end of the spring device 101 is connected to the joint mount 102. Further, the spring device 101 is configured to actuate the joint housing 106 between a first position (shown in FIG. 5A) and a second position (shown in FIG. 5B). As illustrated, the first position corresponds to a compressed position of the spring device 101 and the second position corresponds to an extended position of the spring device 101. In one embodiment, the first and second joints comprise ball joints, or alternatively a rotary joint of at least one degree, and the joint housing 106 provides at least two degrees of freedom to the spar 111.

In some embodiments, as illustrated in FIG. 2, the spring device 101 is connected to a swing arm 104 on the distal end 100B of the device 100 and to a spring joint housing 105 at the proximal end 100A of the device 100. The spring joint housing 105 is coupled to and extending from the joint housing 106. Whereas, the swing arm 104 is coupled to an arm 109, which in-turn is coupled to the joint mount 102, as further discussed below in relation to FIGS. 3-4. In certain embodiments, the swing arm 104 includes a first end and a second end, the first end of the swing arm 104 attached to the second end of the spring device 101, and the second end of the swing arm 104 attached to the joint mount 102 via an arm, the swing arm 104 capable of actuating from a non-extended position when the joint housing 106 is between its first and second positions, to an extended position upon the joint housing 106 reaching the third position, wherein the joint housing 106 reaches a third position upon the swing arm 104 reaching the extended position and the spring device 101 reaching the extended position.

Next, referring to FIG. 3 another perspective view of the lift assistance device 100 coupled to a spar mount assembly 103, as shown in FIG. 2, is shown. Further details illustrated in FIG. 3 include a ball member 108, a latch 107 and a lever 110 (further discussed with respect to FIG. 4). As noted above, the joint mount 102 is coupled to or mates with the joint housing 106. Specifically, as illustrated in FIG. 3, the joint housing 106 includes a cavity therein that receives a ball member 108 extending from the joint mount 102. Such ball member 108 rides against a fixed cup (not shown), is received in the cavity of the joint housing 106 and allows the joint housing 106 to pivot vertically as shown in FIGS. 5A-5C, which in-turn allows spar 111 (shown in FIGS. 6A-6B) to achieve vertical displacement from a ground surface to a certain height above the ground, in addition to allowing the spar 111 to pivot horizontally. Stated differently, the spherical ball member 108 rides against a fixed cup on the proximal end of the joint housing 106. The joint housing 106 also includes a floating brake cup (not shown) that is proximal to the spar 111. The floating brake cup is linearly adjustable. The spherical ball member 108 is connected to the joint mount 102, which in-turn mates with the spar mount assembly 103. The joint housing 106 configured to be coupled to a distal end of the spar 111. The spar 111 being capable of supporting at least one limb of a patient during the surgical procedure. The spring device 101 and the joint mount 102 being distal to the joint housing 106 relative to the spar 111.

The vertical movement of the joint housing 106 results in providing lift assistance to the user by applying a vertical force to the spar 111. Such functionality is achieved by having the spring device 101, attached to the joint mount 102, act against the joint housing 106, thereby resulting in lifting the spar 111 upwards as the joint housing 106 rotates or pivots about the ball member 108 positioned in the cavity formed in the joint housing 106. This lift creates a countering force that at least partially neutralizes the applied moment load of the spar 111 itself with or without the additional weight of the patient.

In one embodiment further illustrated in FIG. 3, the spring joint housing 105 extends from the joint housing 106 and is coupled with the spring device 101, wherein a ball member 101-1 extending from the spring device 101 mates with the spring joint housing 105. Such mating configuration allows for the joint housing 106 to move between different positions as the spring device 101 is actuated from a compressed position (i.e., first position), to an intermediate position (i.e., second position), and finally to a fully extended position (i.e., a third position), as shown in FIGS. 5A-5C. As illustrated in FIG. 3, the ball member 101-1 is received within a cavity formed in the spring joint housing 105, which permits the spring joint housing 105 to pivot and in-turn have the joint housing 106 pivot with respect to the ball member 108 received in the cavity therein. FIG. 3 further illustrates a latch 107 coupled to an arm 109, which in-turn is coupled to the joint mount 102. These features will be further discussed below in reference to FIG. 4.

Next referring to FIG. 4, another perspective view of an embodiment of the device 100 coupled to the spar mount assembly 103, as shown in FIG. 2, is illustrated. This view illustrates the orientation of the swing arm 104 with the arm 109, which thereon includes a latch 107. The latch 107 rests on top of the arm 109. In order to disengage the spar mount assembly 103 from the mount connector 112, and in-turn disconnect the device 100 from the spar mount assembly 103, which is connected to the surgery table, a user may either actuate a lever 110 coupled to the spar mount assembly 103, or alternatively actuate the latch 107 by pushing up on the latch 107 that in turn will engage with lever 110 in order to unlock or disengage the device 100 from the spar mount assembly 103. One skilled in the art would appreciate that the lever 110 includes an internal mechanism (not shown) that provides a locking mechanism such that the mount connector 112 may snap fit into the spar mount assembly 103. The actuation of the lever 110 causes the mount connector 112 to be pulled away, or alternatively disconnect, disengage, or dismount from the spar mount assembly 103.

Next, embodiments shown in FIGS. 5A-5C will be discussed which illustrate different actuation positions of the device 100 between first, second and third positions. One skilled in the art will appreciate that the spring device 101 acts between the joint mount 102, and the joint housing 106. In one embodiment, the spring device 101, is preloaded to approximately at least 450 pounds when fully extended (shown in FIGS. 5B and 5C), which may be the nominal force for a fully extended spring device 101. The force increases as the spring device 101 is compressed from an intermediate position (FIG. 5B), or alternatively fully extended position (FIG. 5C), to a fully compressed position (FIG. 5A). The entire mechanism of the spring device 101 and first joint being distal to the spar 111 itself, and thus such configuration of the device 100 has no effect upon the x-ray imaging zone. In other words, the spar 111 includes a flange coupled to the joint housing 106, wherein the joint housing 106, joint mount 102, the first joint and the spring device 101 are distal to the metal flange relative to the spar. The positioning of the joint mount 102, the joint housing 106 and the spring device 101 with respect to the flange and the spar itself causes no effect on x-ray imaging and does not impede radiolucency of the spar 111. Because all these features are distal to the flange in relation to the spar 111, these features are not in the field of view when imaging e.g. the leg of the patient adjacent to the spar 111. In certain embodiments, the spar 111 itself is made of carbon fiber or another material that does not impede radiolucency and allows images to be taken of the patient's leg while on the table, e.g. from an x-ray device.

In certain embodiments, the spring device 101 provides positive lift for a user as the spar 111 is raised and/or lowered through the clinically applicable range of motion (approximately +14 degrees to approximately −36 degrees). If the spar 111 needs to be raised higher (up to approximately +28 degrees), the mechanism may include a swing arm 104 that enables the joint housing 106 to be raised further past the second position that corresponds to full extension of the spring device 101. That is, the first portion of the joint housing 106 corresponds to a spar angle of about −36 degrees and the second position of the joint housing 106 corresponds to a spar angle of about 14 degrees, and the third position of the joint housing 106 corresponds to a spar angle of about 28 degrees. One skilled in the art will appreciate that the aforementioned angle measurements are with respect to an x-axis in the same plane as the surface of the surgery table such that the x-axis runs parallel to the surface of the surgery table.

In certain embodiments, the movement between the second and third position by movement of the swing arm 104 is not assisted, and in other embodiments, it is assisted. As illustrated in FIGS. 5A-5C, swing arm 104 includes two bolts, which in certain embodiments are shoulder bolts which are clevis pins that assist in their rotation. Swing arm 104 rotates with respect to the spring device 101 and with respect to the arm 109. In certain embodiments, the swing arm moves with one degree of freedom such that the spring device 101 remains parallel to e.g. the mount connector 112 throughout the movement of the spring device 101 and swing arm 104. The swing arm 104 allows the joint housing 106 to be raised vertically to the third position while having a spring device 101 of a shorter length than would otherwise be necessary. Stated differently, in FIG. 5A, the spring device 101 is fully compressed while the swing arm 104 is fixed or in a non-extended position. In this configuration, the spar 111 is down at approximately −36 degrees with respect to the plane of the surgery table. With respect to FIG. 5B, in the intermediate position (the second position of the joint housing 106), the spring device 101 is fully extended while the swing arm 104 is fixed or in a non-extended configuration. In this configuration, the spar 111 is about 14 degrees with respect to plane of the surgery table. And, finally, in FIG. 5C, the spring device 101 is in a fully extended position while the swing arm 104 is also in an extended position. Such extended position of the swing arm 104 is achieved by having the swing arm 104 rotate about a joint with respect to arm 109. The swing arm 104 is coupled to the arm 109 via a clevis pin or other joint that allows the swing arm 104 to rotate from a fixed position to a non-fixed or an extended position. In this configuration the spar 111 is about 28 degrees with respect to the plane of the surgery table. The actuation of the swing arm 104 is unassisted, or alternatively the actuation of the swing arm 104 is assisted, for example, by a pivoting joint using a link mechanism, cam mechanism, gears, springs and other similar mechanisms. The link mechanisms may include two or more moving links, slider-crank mechanism, or crank and piston mechanism. The cam mechanism may include rotating cam coupled with a translating or rotating following. Gears may include rack and pinion mechanism, ordinary gear trains, and planetary gear train. For certain embodiments where the swing arm 104 is unassisted, once the user lifts the spar 111 beyond the second position, the spring device 101 provides no additional lift assistance to the user, requiring the user to provide any force necessary to move the joint housing 106 and attached spar 111 from second position to third position. In certain embodiments, the spring device 101 is still preloaded to ~450 pounds (approximately); however, when fully extended, the spring device 101 contacts its internal hard stop.

Stated another way, the swing arm 104 includes a first end and a second end. The first end of the swing arm 104 being attached to the second end of the spring device 101, and the second end of the swing arm 104 being attached to the joint mount 102 via an arm 109. In certain embodiments, the connection of the swing arm 104 is a rotational joint with respect to the spring device 101 and the arm 109. The swing arm 104 being capable of actuating from a non-extended position (illustrated in FIGS. 5A-5B) to an extended position (illustrated in FIG. 5C) upon the joint housing 106 reaching the second position (illustrated in FIG. 5B). The joint housing 106 reaches a third position (illustrated in FIG. 5C)

upon the swing arm 104 and the spring device 101 reaching their respective extended positions. Stated in another way, one skilled in the art will appreciate that the joint housing 106 in the first position corresponds to the spring device 101 being fully compressed; the joint housing 106 in its second position corresponds to the spring device 101 in its fully extended position; and the joint housing 106 in the third position corresponds to the spring device 101 in the fully extended position and the swing arm 104 in an extended position as shown in FIG. 5C. One skilled in the art will appreciate that the joint housing is operable in a range of positions from first to second position, and from second to third position. In certain embodiments, the joint housing may be maintained at a position in the range between such positions, for example, by use of brake, for example, the floating brake cup discussed herein.

Still referring to FIGS. 5A-5C, one skilled in the art would appreciate that as the spring device 101 goes from a fully compressed configuration (FIG. 5A) to a fully extended configuration (FIG. 5C), and thereby the joint housing 106 pivots about the ball member 108 and the spring joint housing 105 pivots about the ball member 101-1, the mount connector 112 and the joint mount 102 maintain their alignment with respect to each other, and potentially the spar mount assembly 103 if the same is coupled and engaged with the mount connector 112. That is, joint mount 102 maintains alignment with the spar mount assembly 103 while the joint housing 106 pivots between the first and second positions. In certain embodiments, the first and second joint comprise ball joints, or alternatively a rotary joint of at least one degree, wherein the second joint couples the spring device 101 and the joint housing 106 includes a cavity therein, as discussed above with respect to FIG. 2. The joint housing 106 capable of pivoting with respect to the ball member 108 positioned in the cavity of the joint housing 106. The pivoting of the joint housing 106 between the first and second positions is caused by actuating the proximal end of the spar 111, the distal end of the spar 111 capable of being maneuvered by a user from proximal end of the spar 111. In addition to the vertical movement of the spar 111 that is assisted by the spring device 101, the user is also able to move the spar horizontally through movement of the joint housing 106 with respect to the ball member 108 and the ball member 101-1, allowing the spar 111 to move in at least two degrees of freedom.

In certain embodiments, the spar 111 connected to the joint housing 106 moves in at least two degrees of freedom from a single axis defined by the first joint, which in certain embodiments includes a ball joint, or alternatively a rotary joint of at least one degree. The spar 111 and connected device 100 does not require multiple axes defined by multiple joints in order to achieve at least two degrees of freedom of the spar 111.

Figure 6A:
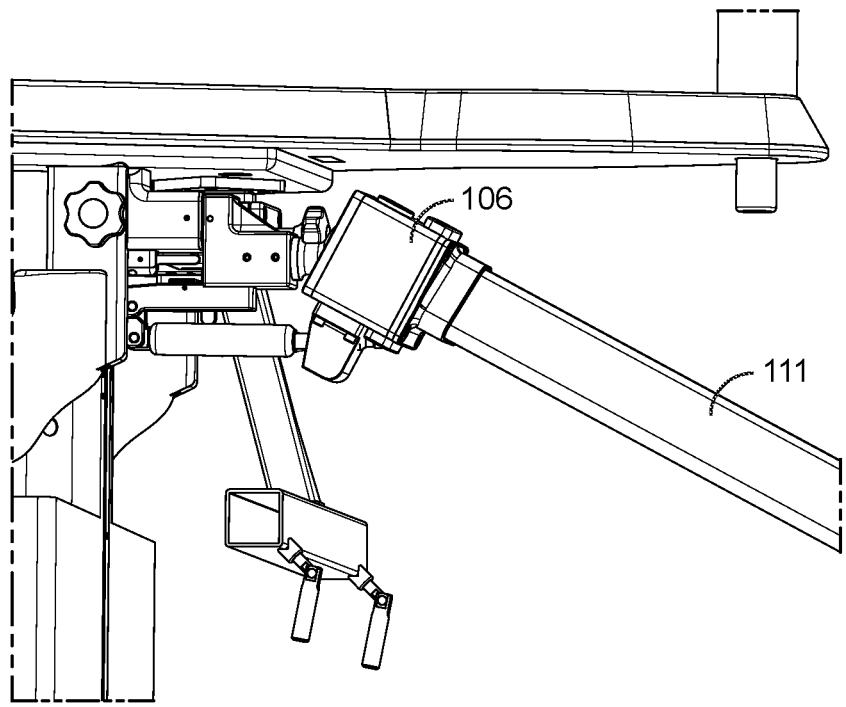
FIG. 6A is a perspective view of the lift assistance device coupled to the surgery table according to an example embodiment.
Figure 6B:
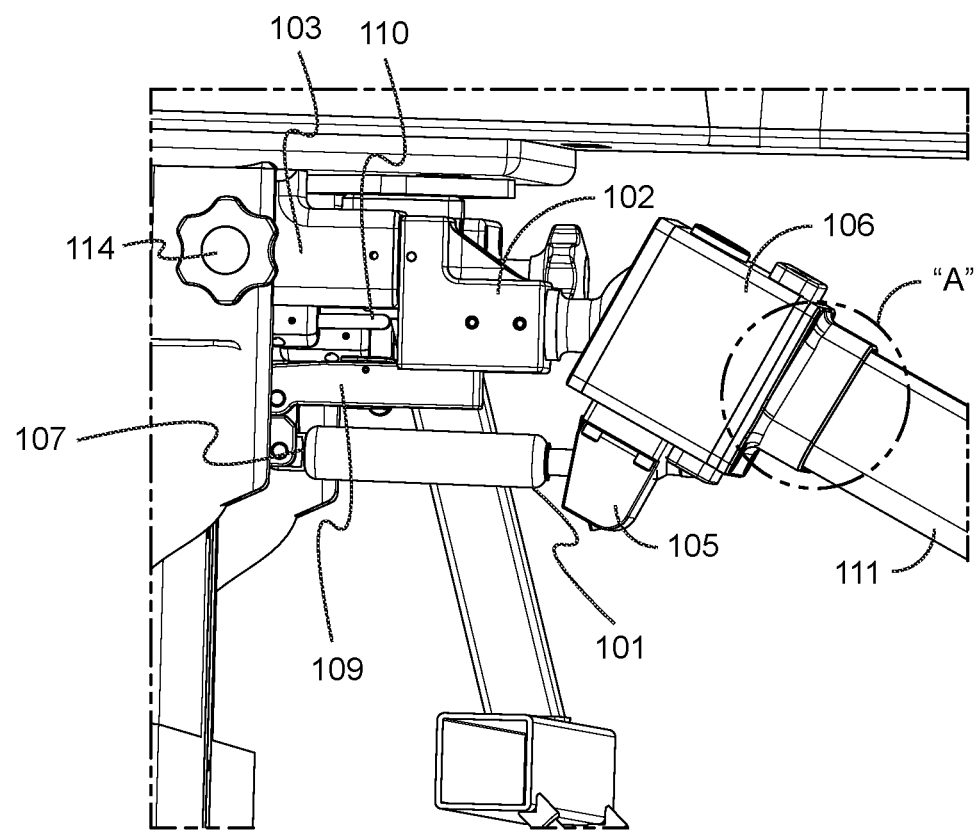
FIG. 6B is a closer view of the lift assistance device illustrated in FIG. 6A.

Next referring to FIGS. 6A-6B, perspective views of an embodiment of the device 100 coupled to the surgery table according to an example embodiment are illustrated. FIG. 6B is a closer view of FIG. 6A which illustrates the device 100, with accompanying different components (i.e., joint housing 106, joint mount 102, spring device 101, and mount connector 112 (not shown)) being engaged or coupled with the spar mount assembly 103. Additionally, FIG. 6B illustrates a locking or tightening knob 114 coupled to the surgery table and the device 100; and annotation "A" representing a fitting end of the spar 111. This fitting end "A" defines the distal end of the x-ray imaging zone that does not have any metal present.

Figure 7A:
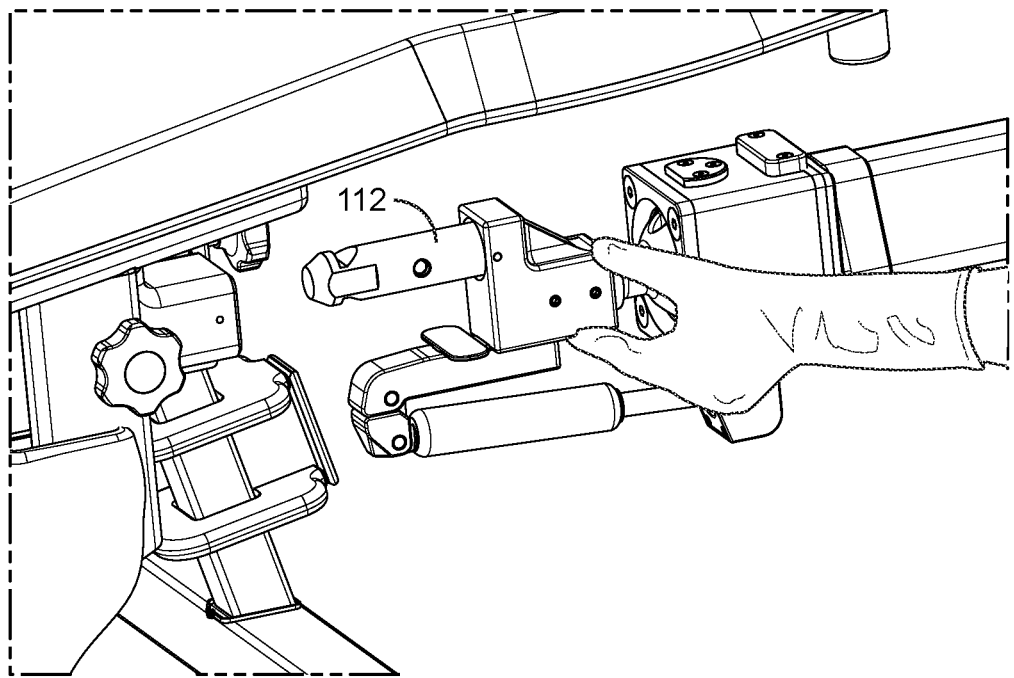
FIGS. 7A-7C are perspective views of engaging a spar to a spar mount assembly and locking the same in place according to an example embodiment.
Figure 7B:
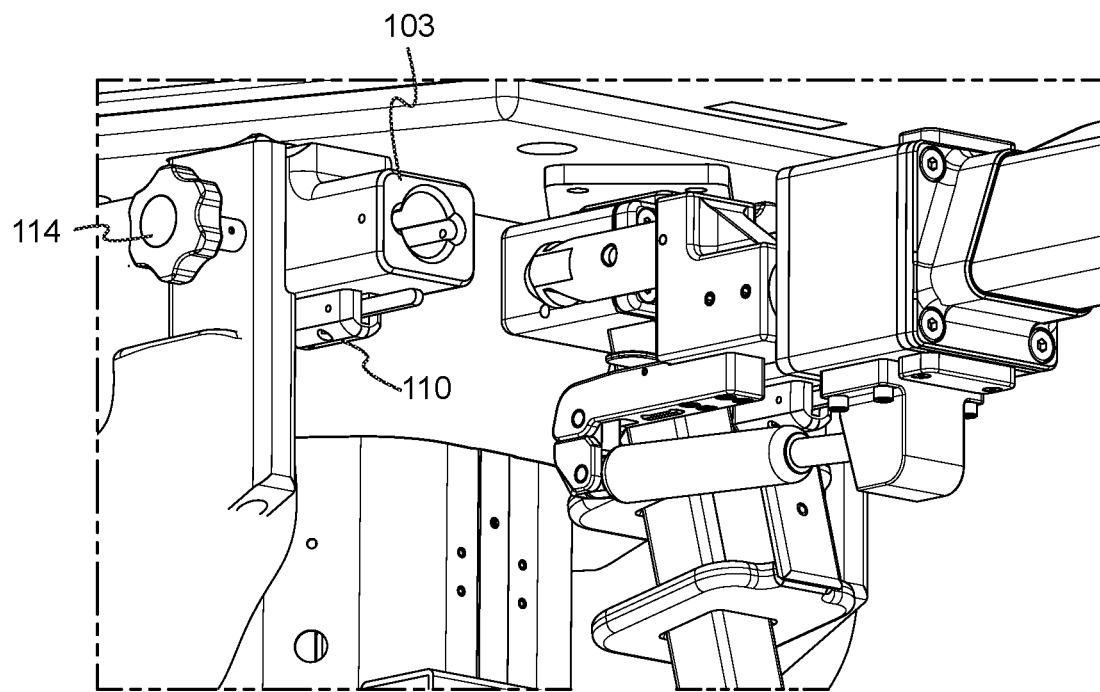
Figure 7C:
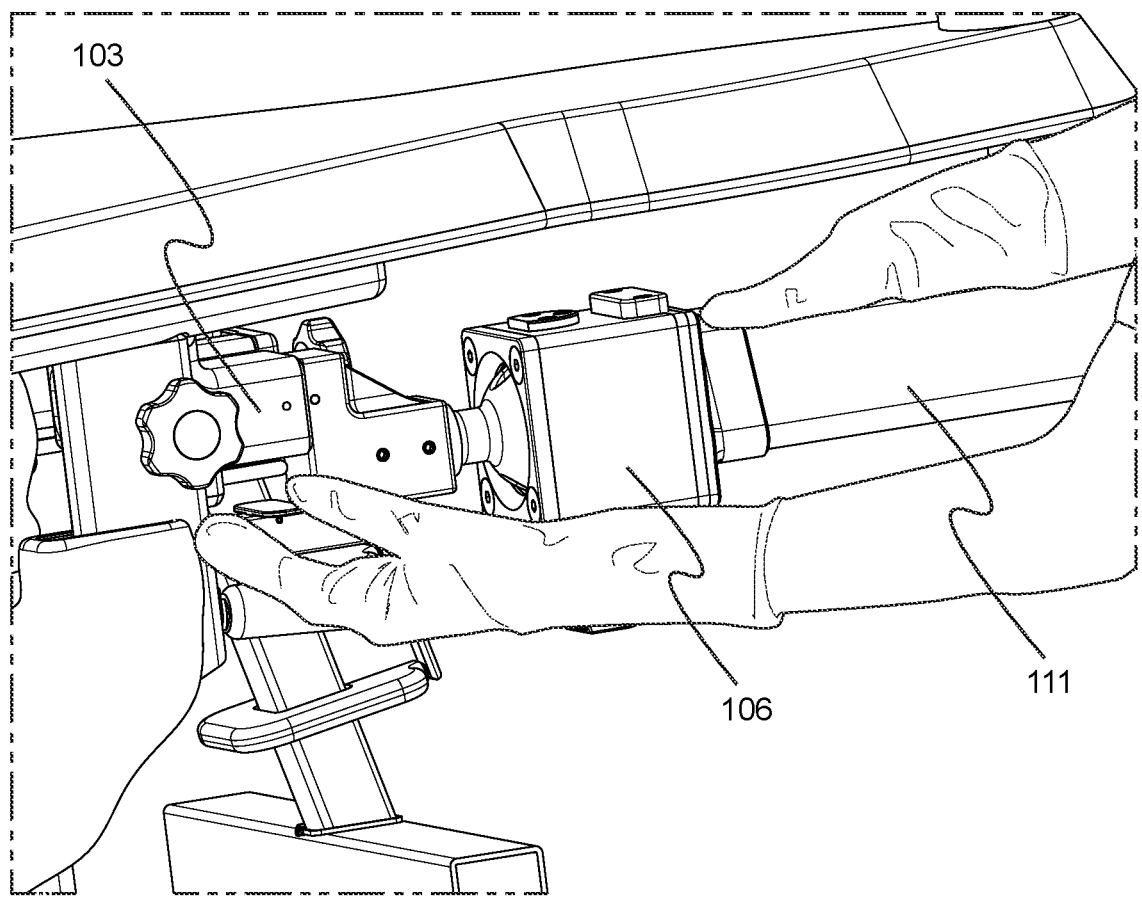
Figure 13:
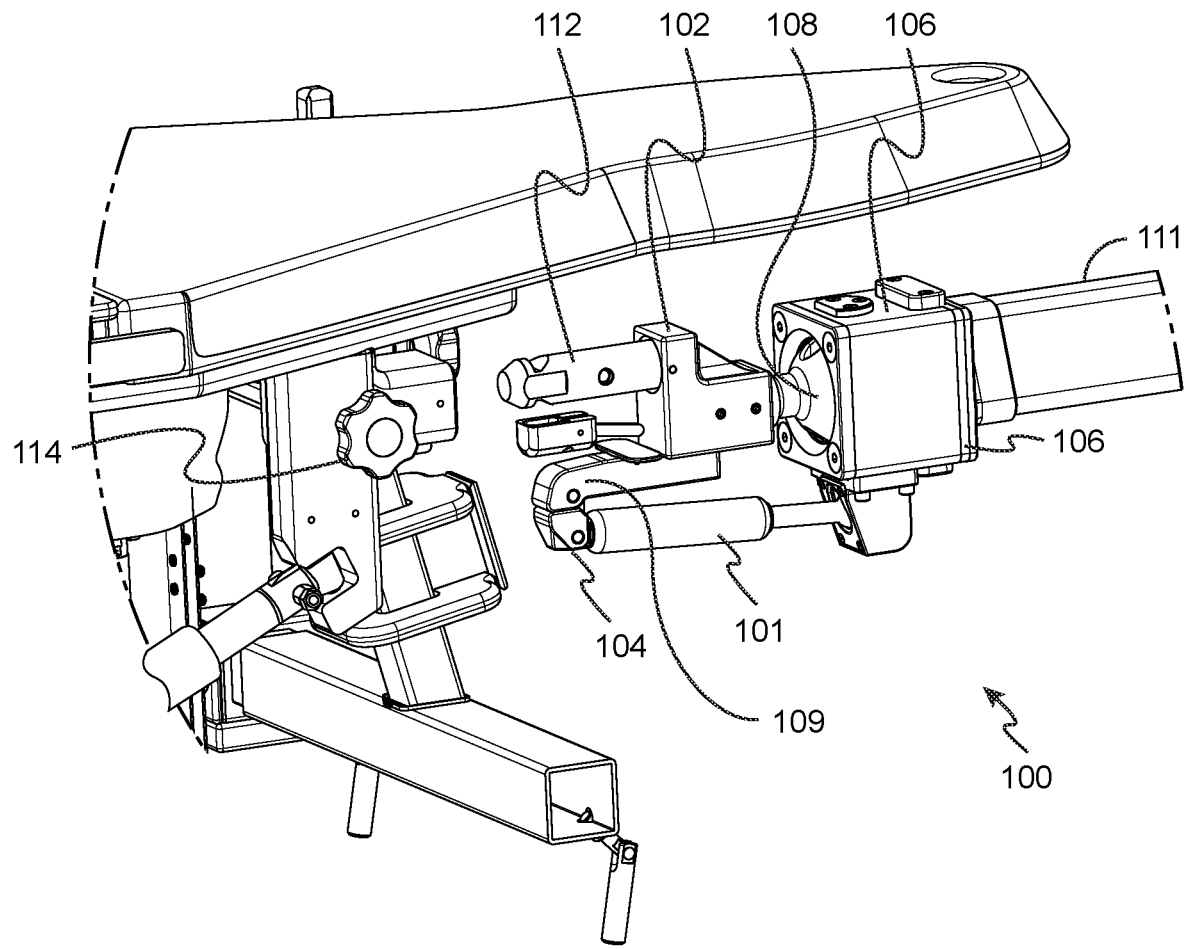
FIGS. 13-15 illustrate the method of engaging a spar to a spar mount assembly, wherein the spar being coupled to a lift assistance device illustrated in either FIGS. 2-3 or FIG. 8, and the spar mount assembly being coupled to a surgery table.
Figure 14:
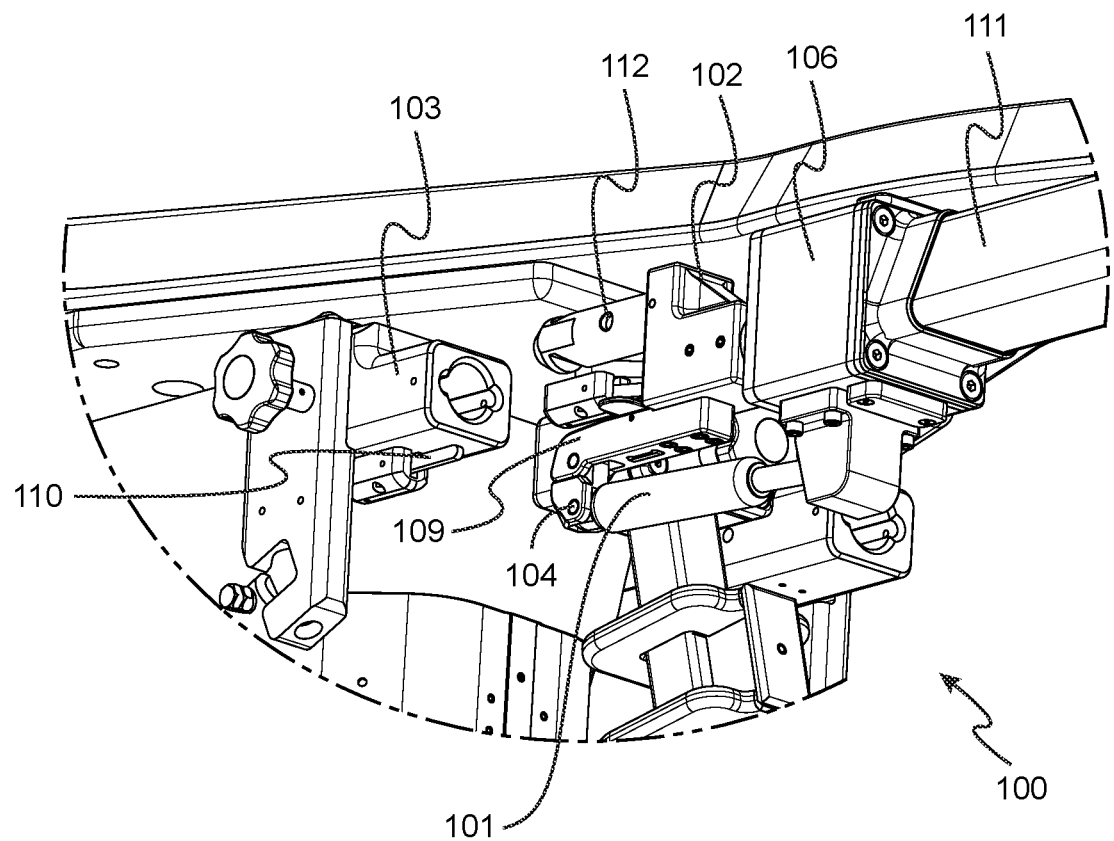
Figure 15:
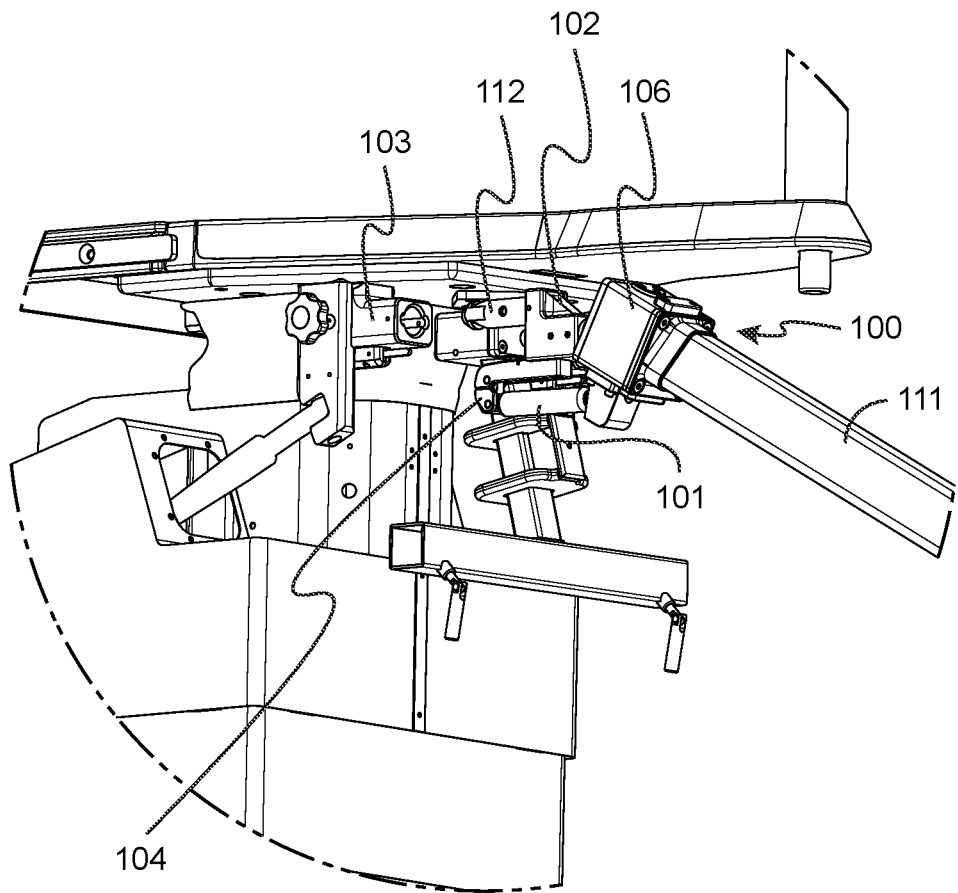
Figure 16:
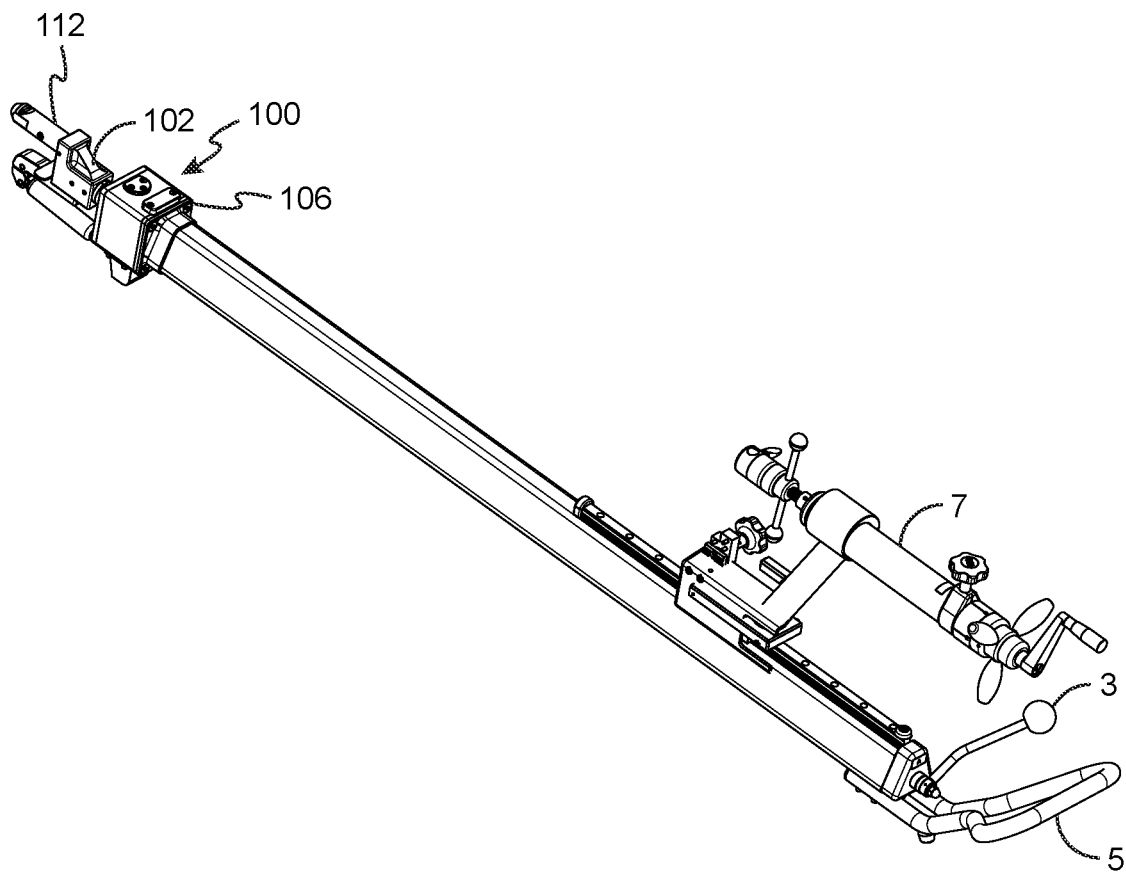
FIGS. 16-20 illustrate different perspective views of the lift assistance device coupled to brake handle, user grip, and articulation joint that are coupled to a respective spar.
Figure 17:
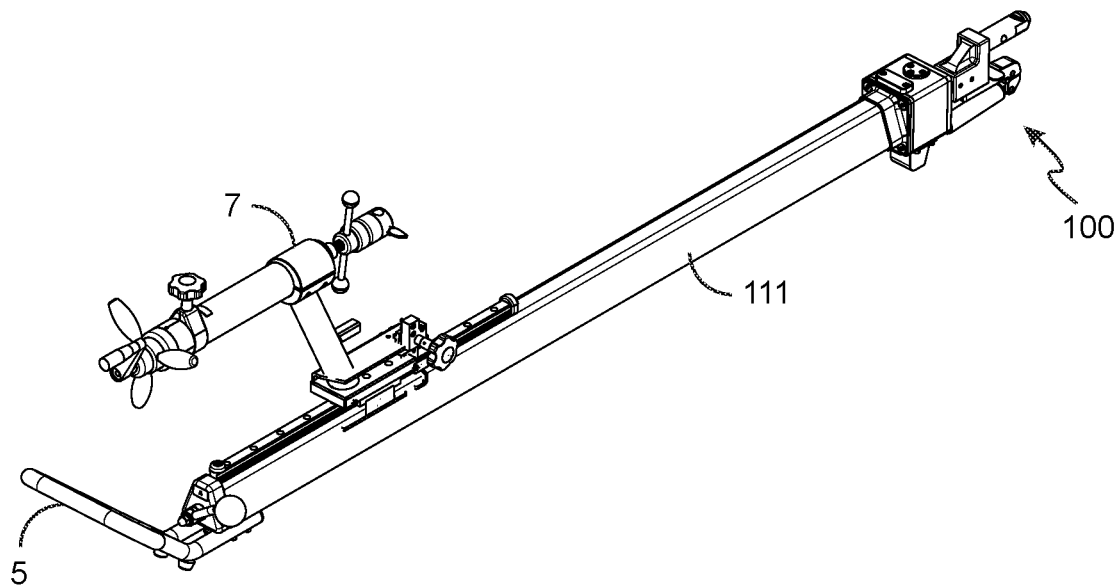
Figure 18:
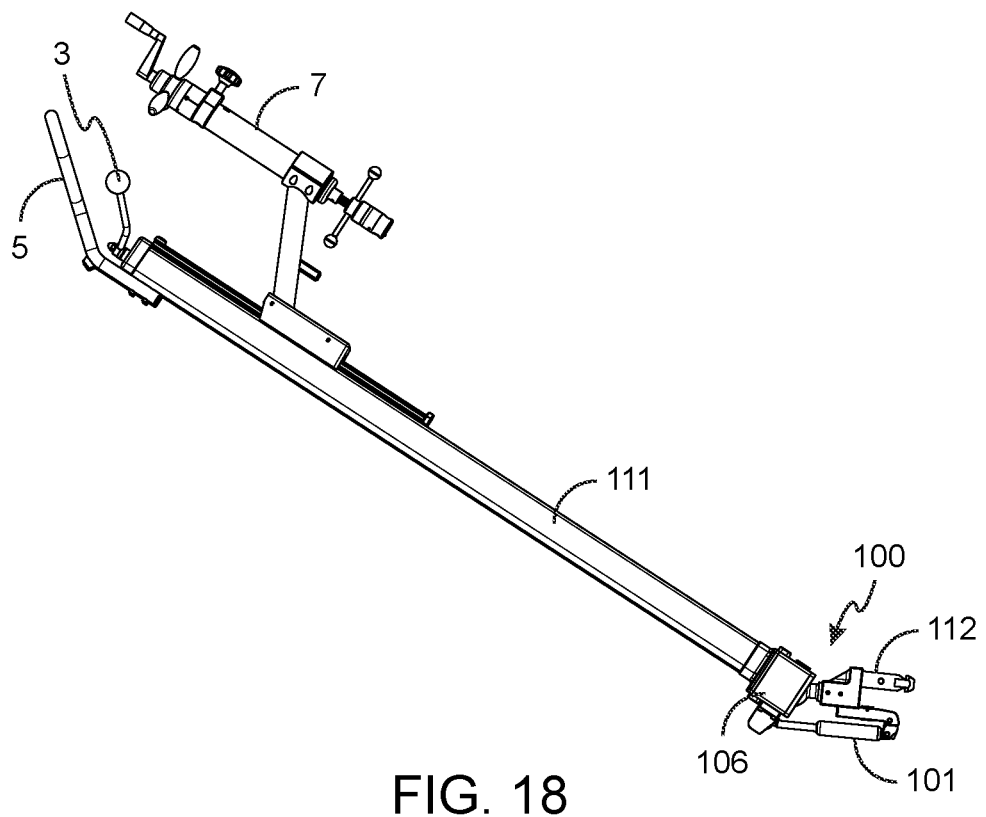
Figure 19:
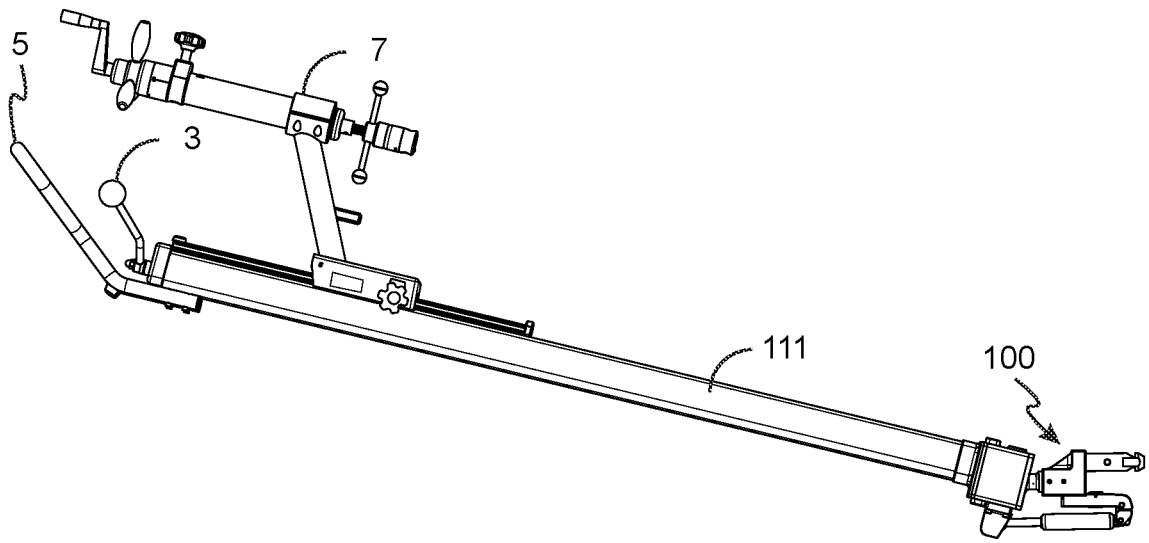
Figure 20:
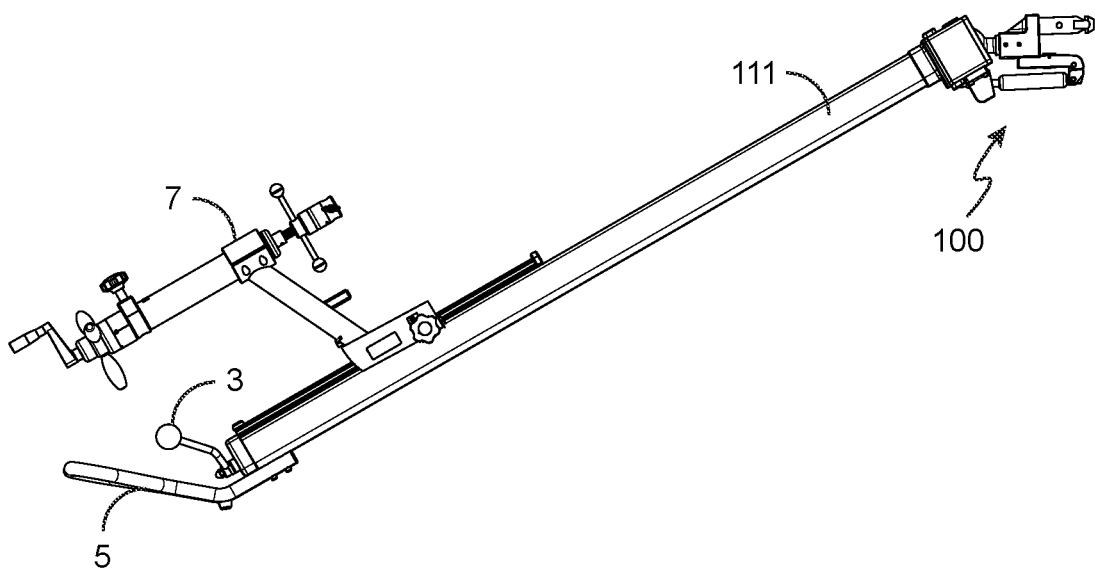
Figure 21:
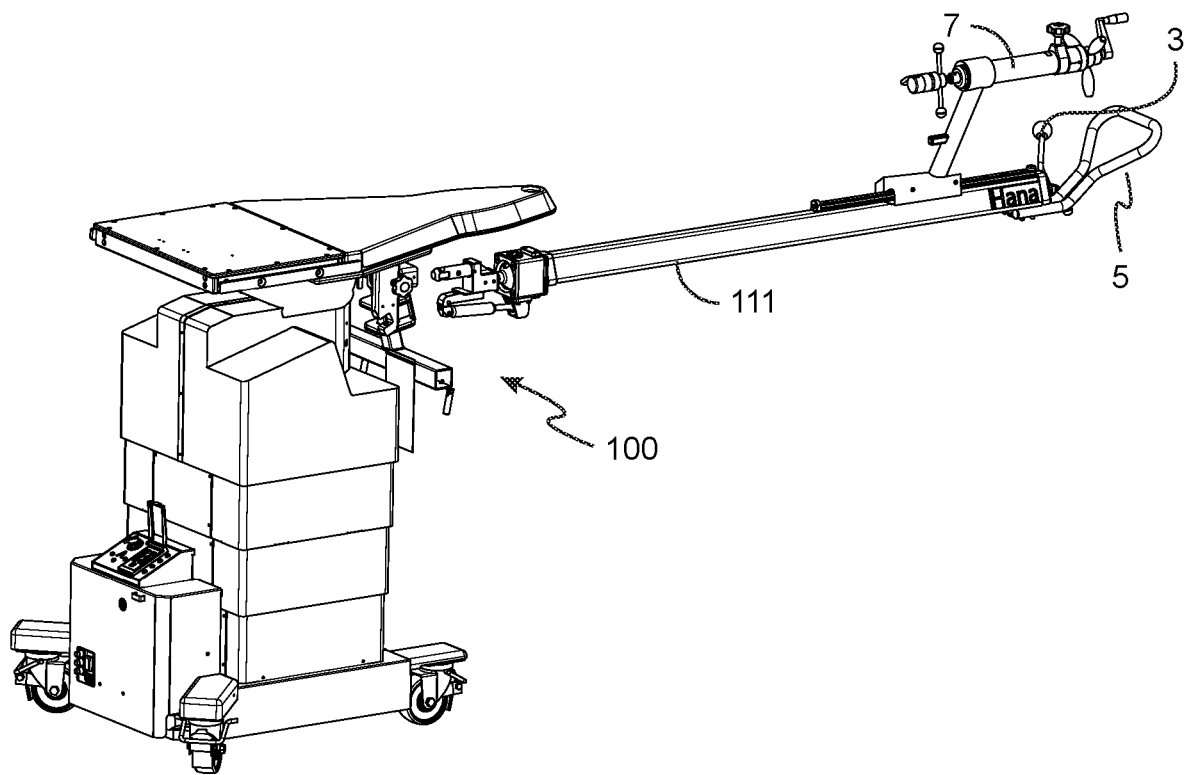
FIGS. 21-24 illustrate different perspective views of the system with respective spars being coupled to lift assistance device illustrated in either FIGS. 1A-B, 2-3 or FIG. 8.
Figure 22:
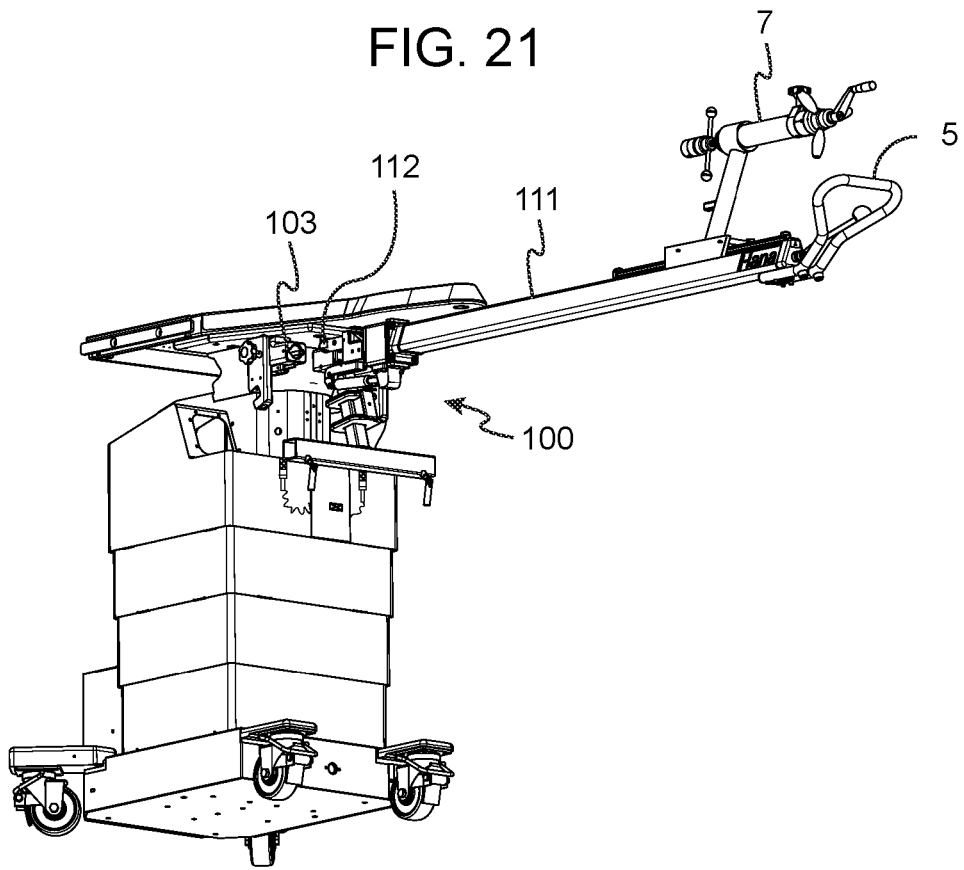
Figure 23:
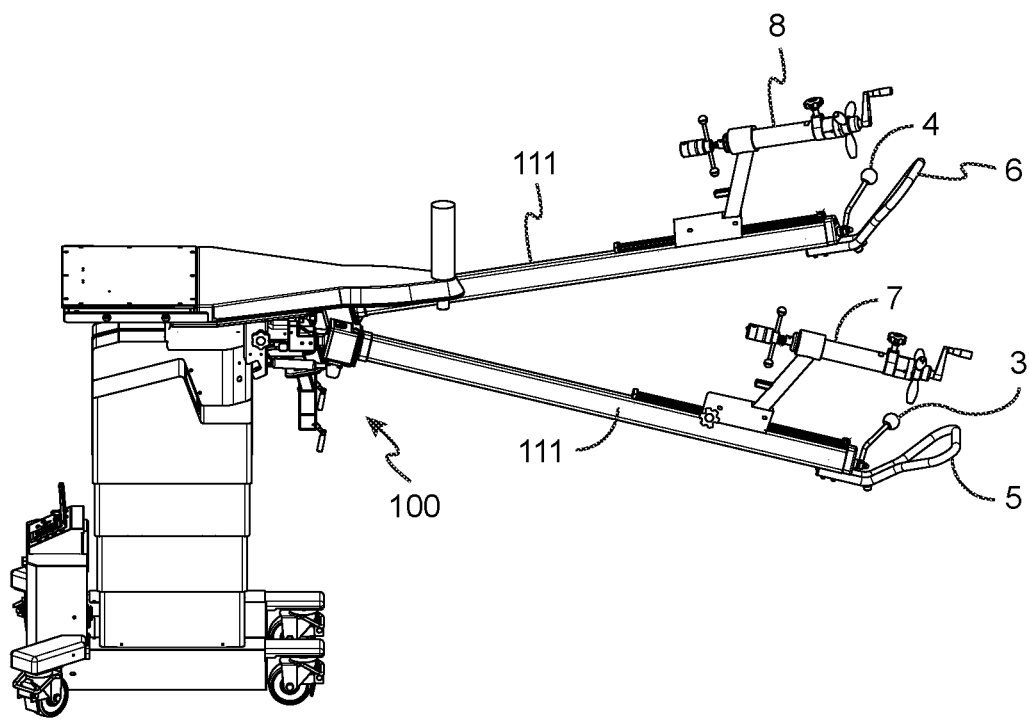
Figure 24:
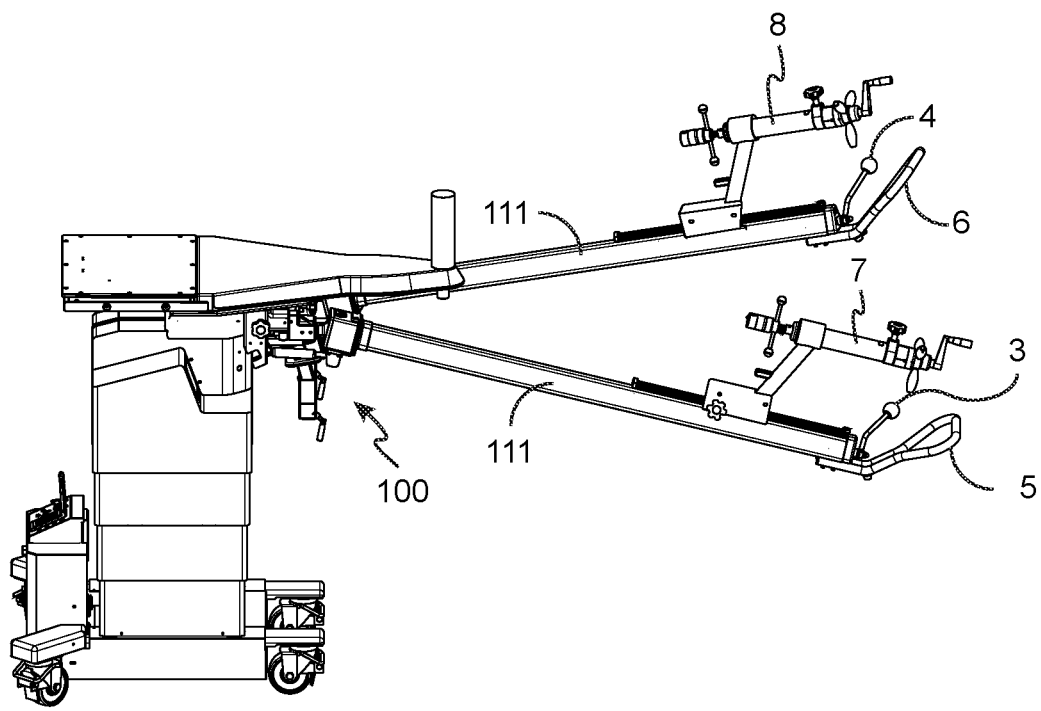

FIGS. 7A-7C illustrates perspective views of engaging an embodiment of a spar 111, to a spar mount assembly 103 and locking the same in place. FIGS. 13-15 illustrate similar views of a spar 111 illustrated in FIGS. 1A-1B. One skilled in the art would appreciate that the spars 111 are designed to be removable from the surgery table to make storage and table transportation easier. An assembly of the spar 111 and the spar mount assembly 103 may be achieved by first having the spar 111 engage with the spar mount assembly 103. As shown in FIG. 7B, the spar mount connector 112 is positioned to be placed into the spar mount assembly 103. The spar mount assembly 103 is affixed to the surgery table and includes a cavity therein to receive the mount connector 112. The mount connector 112 engages and mates with the spar mount assembly 103 in order to hold the spar 111 in place relative to the surgery table. Further illustrated in FIG. 7B, the spar mount assembly 103 includes a lever 110 disposed underneath, which may be actuated by a user to release the spar 111, if needed.

Once the spar 111 is in place and locked into the spar mount assembly 103, a locking knob 114 may be actuated by turning the locking knob 114 clockwise until tight. The spar 111 may be maneuvered up and down while tightening the locking knob 114 to ensure the spar 111 is securely and firmly positioned. Additionally, the user may rotate the respective brake handle 3, 4 in order to have a floating brake cup (not illustrated) to be driven linearly into a spherical ball, thereby creating sufficient holding torque to support the spar 111 from dropping to the ground. When the respective brake handle 3, 4 is rotated in the counterclockwise direction, the floating brake cup releases and the spar 111 is free to be adjusted up or down or outwards/inwards (abduction/adduction).

Figure 8:
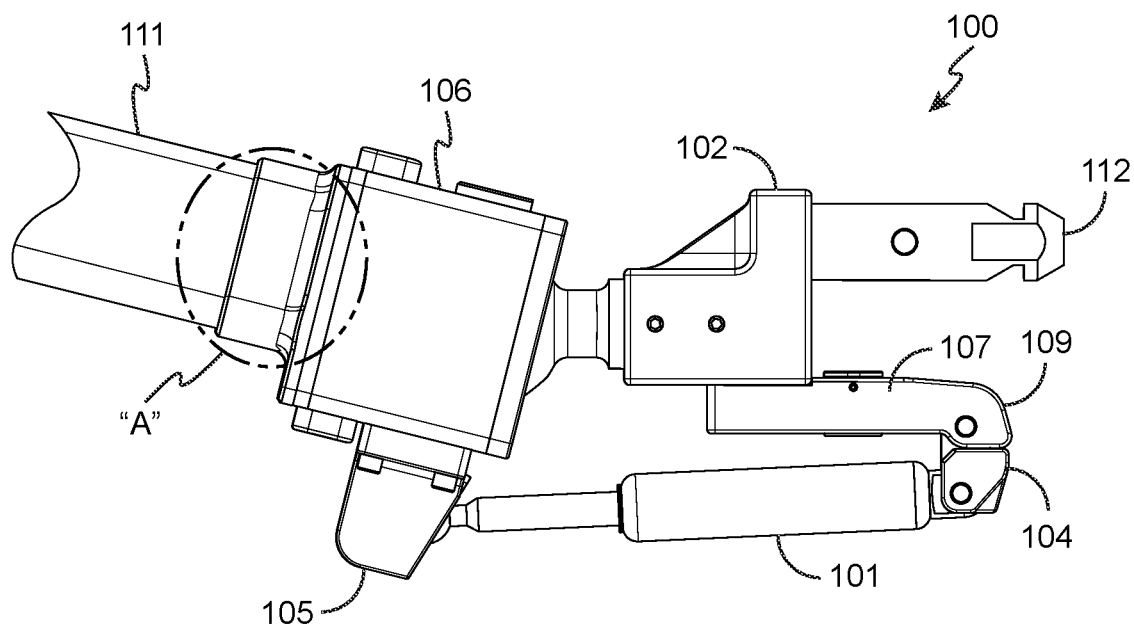
FIGS. 8-12 illustrates perspective views of the device according to another example embodiment.
Figure 9:
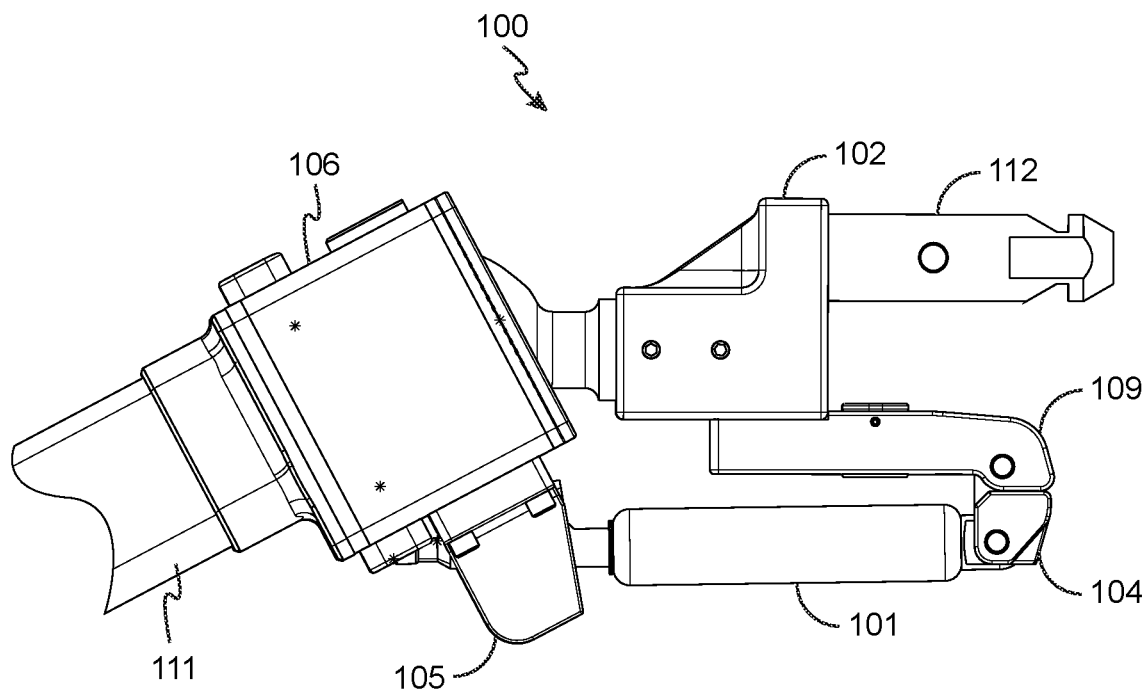
Figure 10:
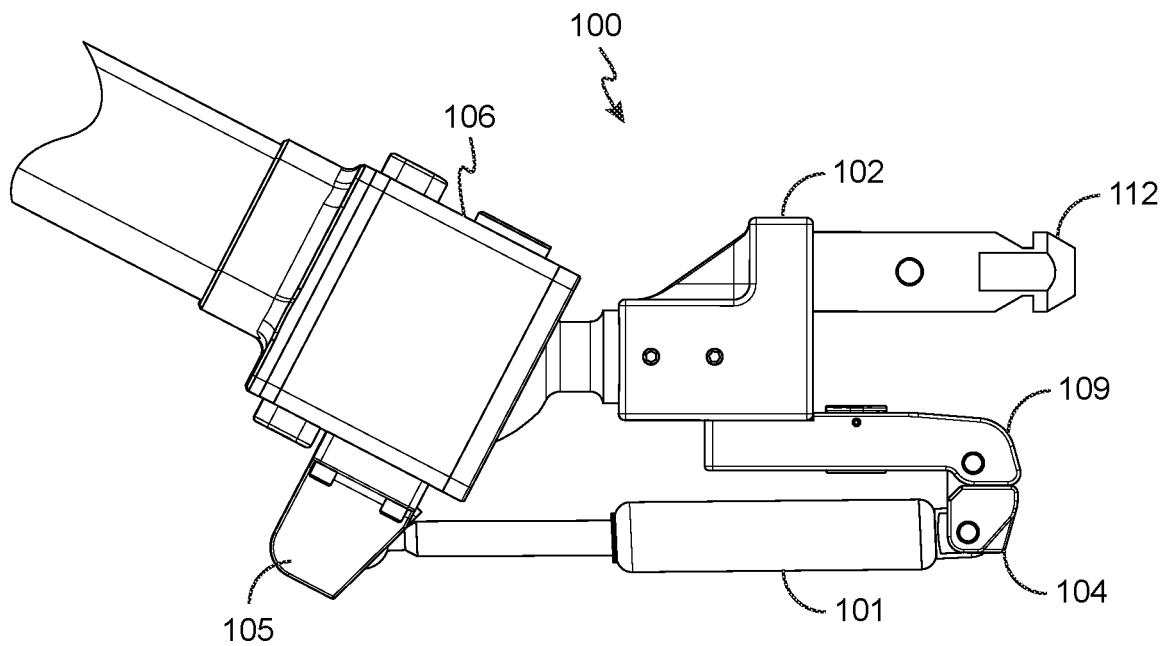
Figure 11:
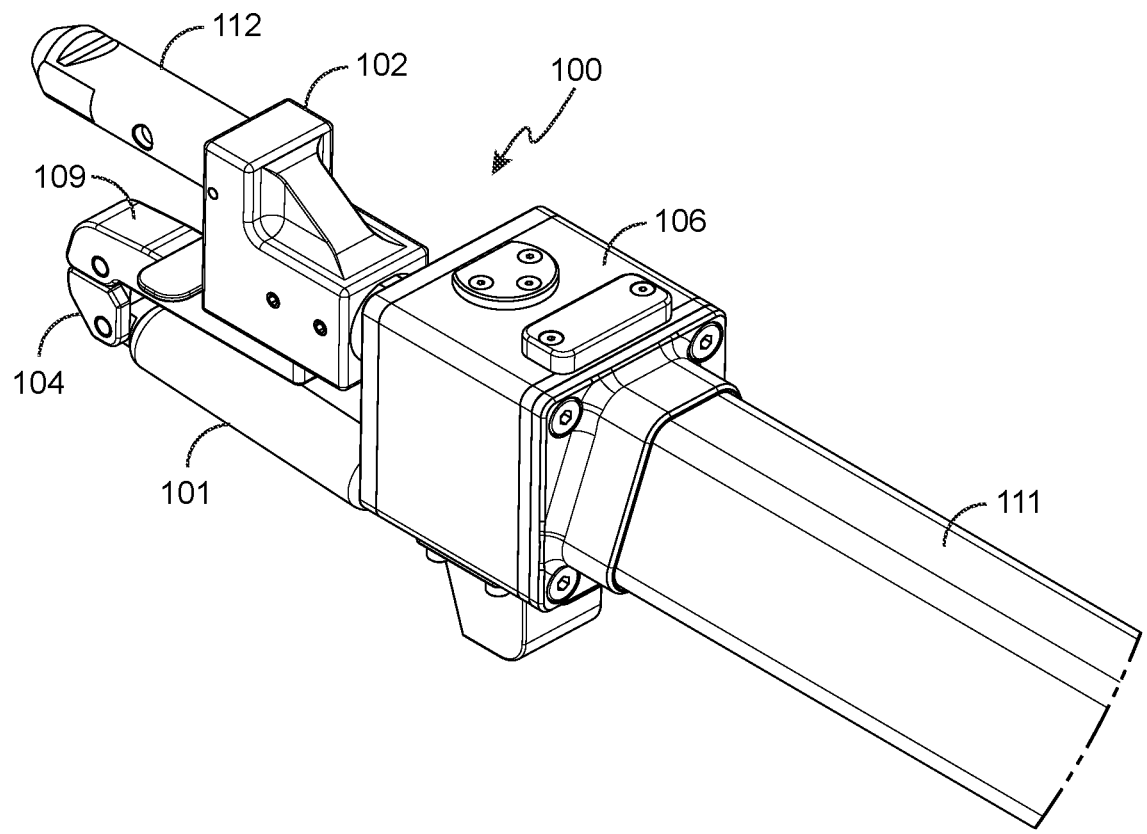
Figure 12:
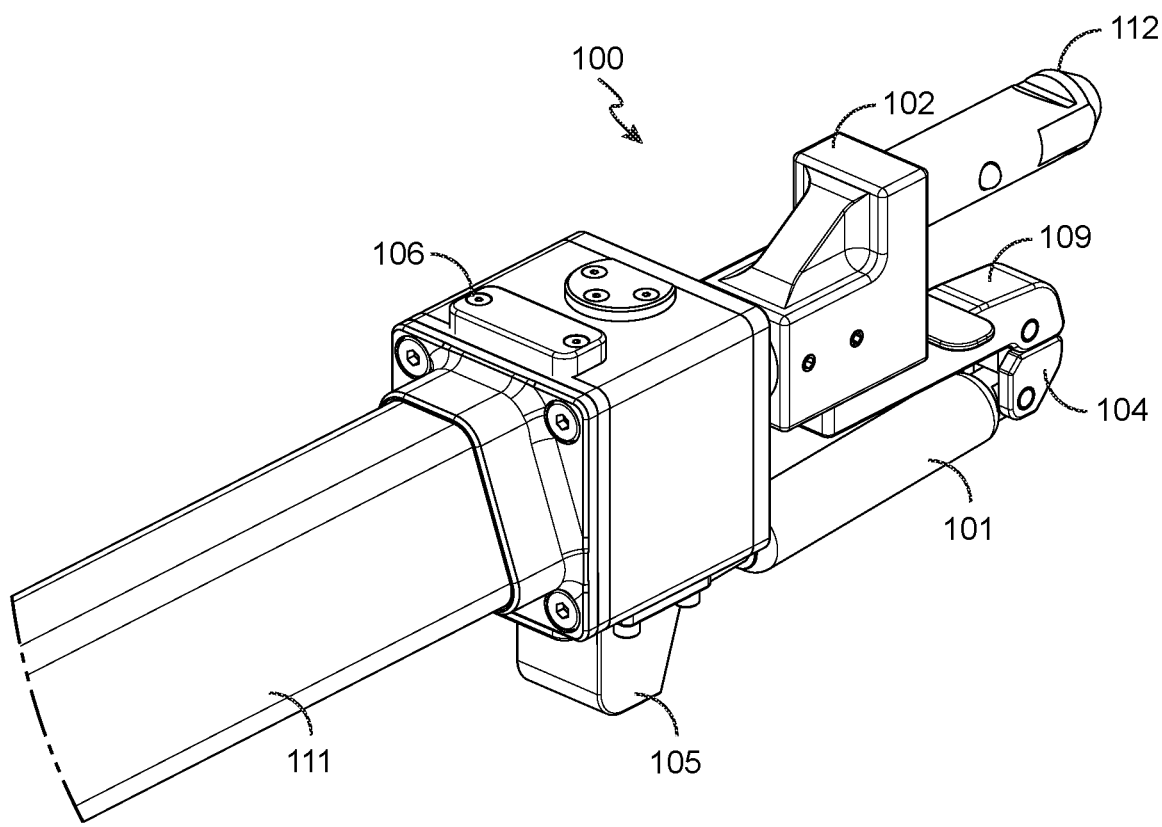

FIGS. 8-12 illustrates perspective views of another example embodiment of the device 100 is shown. According to this example embodiment, unlike the latch 107 illustrated in FIGS. 2-3, the latch 107 illustrated in FIG. 8 is embedded in arm 109 in a slot mechanism fashion. That is, instead of being on top of the arm 109 as illustrated in FIGS. 2-3, the latch 107 is in a slot mechanism form that is built inside or incorporated in the arm 109 itself. Further, as illustrated, annotation "A" represents a fitting end of the spar 111. This fitting end "A" defines the distal end of the x-ray imaging zone that does not have any metal present. FIGS. 8-12 illustrate an embodiment of the device 100 similar to the embodiment of the device 100 illustrated in FIGS. 2-4 and 5A-5C, wherein mechanism, structural configuration and orientation of the device 100 are consistent between the two embodiments, with one difference being with respect to latch 107 feature as noted above.

FIGS. 13-15 illustrate the method of securing an embodiment of the device 100 along with a spar 111 coupled thereto to a surgery table. In particular, these figures are similar to what is discussed above with respect to FIGS. 7A-7C and the accompanying disclosure in regards to mounting a spar 111 to a spar mount assembly 103 coupled to the surgery table. However, unlike FIGS. 7A-7C, the spar 111 being mounted to the spar mount assembly 103 in FIGS. 13-15 includes an embodiment of the device 100 coupled thereto. This device 100 may be either device illustrated in FIG. 2-3 or alternatively device illustrated in FIG. 8. With the attachment or coupling of the device 100 to the spar 111, as shown in FIGS. 13-15, provides the user with assisted articulation in maneuvering the spar 111.

FIGS. 16-20 illustrate different perspective views of an embodiment of the device 100 coupled to a respective brake handle 3, 4, a user grip 5, 6, and a respective articulation joint 7, 8 that are coupled to a respective spar 111, in a similar fashion as illustrated in FIGS. 1A-1B above. In particular, the brake handle 3, 4, a user grip 5, 6, and a respective articulation joint 7, 8 being coupled to the respective spar 111 as illustrated in FIGS. 1A-1C, now include and embodiment of the device 100 at distal end of the respective spar 111. The device 100 may be either device 100 illustrated in FIG. 2-3 or alternatively device 100 illustrated in FIG. 8.

FIGS. 21-24 illustrate different perspective views of an embodiment of the system as shown in FIGS. 1A-1B above with the addition of an embodiment of the device 100, wherein the device 100 may be either device 100 illustrated in FIG. 2-3 or alternatively device 100 illustrated in FIG. 8. In other words, one skilled in the art will appreciate that the system comprising the surgery table, the leg support spar device, and components thereof, shown in FIGS. 1A-B correspond to representations illustrated FIGS. 21-24. FIGS. 21-24 particularly highlight the inventive concepts disclosed herein pertaining to inter alia, the brake handles 3, 4; user grips 5, 6; and articulation joints 7, 8. Moreover, FIGS. 23-24 incorporate features illustrated in FIGS. 1A-B such as, foot pedal, a support member extending perpendicular to the floor, and a hook-shaped engagement member extending from the support member to engage with in support of a user's thigh, for instance. As illustrated, two different spars 111 are illustrated that assist in lifting a patient's respective limb (i.e., right leg or left leg) in order to perform surgery, such as hip related surgeries or lower limb orthopedic procedures. Each of the respective spars are independent of each other such that their movement can be controlled independently by a user or technician. One spar may be in a downward position whereas the other spar may be in an upward position. The respective spar 111 is connected to a respective spar mount assembly 103 positioned below the surgery table such that each respective spar 111 has its own respective spar mount assembly 103. This allows independent movement and control of each one of the respective spars 111. One skilled in the art would appreciate that although two spars 111 are illustrated in FIGS. 1A-1C and FIGS. 21-24, additional spars may be mounted to the surgery table for example; to support other limbs such as arms or patients head.

It should be noted that in certain embodiments the downward moment load of the spar varies substantially with the linear position of the traction assembly, and the weight of the patient's leg. Therefore, it is possible that a spring device will not provide neutral compensation in all cases, however, the effort from the user to raise and lower the spar will be reduced. In certain embodiments, the force of the gas spring can be preset to provide as much lift as desired.

It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open-ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least"; the term "such as" should be interpreted as "such as, without limitation"; the term 'includes" should be interpreted as "includes but is not limited to"; the term "example" is used to provide exemplary instances of the item in discussion, not an exhaustive or limiting list thereof, and should be interpreted as "example, but without limitation"; adjectives such as "known," "normal," "standard," and terms of similar meaning should not be construed as limiting the item described to a given time period or to an item available as of a given time, but instead should be read to encompass known, normal, or standard technologies that may be available or known now or at any time in the future; and use of terms like "preferably," "preferred," "desired," or "desirable," and words of similar meaning should not be understood as implying that certain features are critical, essential, or even important to the structure or function of the present disclosure, but instead as merely intended to highlight alternative or additional features that may or may not be utilized in a particular embodiment.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. The terms "about" or "approximate" and the like are synonymous and are used to indicate that the value modified by the term has an understood range associated with it, where the range may be ±20%, ±15%, ±10%, ±5%, or ±1%. The term "substantially" is used to indicate that a result (e.g., measurement value) is close to a targeted value, where close may mean, for example, the result is within 80% of the value, within 90% of the value, within 95% of the value, or within 99% of the value. Also, as used herein "defined" or "determined" may include "predefined" or "predetermined" and/or otherwise determined values, conditions, thresholds, measurements, and the like.

What is claimed is:

1. A lift device for providing lift assistance for a surgical procedure, comprising:
   a joint housing comprising a cavity configured to receive a ball member configured to pivot the joint housing, the joint housing coupled to a surgical table and to a distal end of a spar configured to support at least one limb of a patient for the surgical procedure; and
   a spring device coupled to the joint housing, the spring device being distal to the joint housing relative to the spar, and the spring device configured to actuate the joint housing in a range between a first position and a second position, the first position corresponding to a compressed position of the spring device, the second position corresponding to an extended position of the spring device.

2. The lift device of claim 1, further comprising a spring joint housing disposed between the joint housing and the spring device,
   wherein the spring device is configured to actuate the spring joint housing to actuate the joint housing.

3. The lift device of claim 2, wherein the spring joint housing is distal to the joint housing relative to the spar.

4. The lift device of claim 1, wherein the spring device is aligned with the spar.

5. The lift device of claim 1, wherein the spring device comprises a single gas spring.

6. The lift device of claim 1, wherein the spring device is below the spar.

7. The lift device of claim 1, further comprising a swing arm coupled to the joint housing, the swing arm configured to actuate from a non-extended position to an extended position,
 wherein the swing arm is configured to maintain the non-extended position as the joint housing transitions between the first position and second position as the spar is raised with respect to a plane of the surgical table, and
 wherein the swing arm is configured to actuate from the non-extended position to the extended position when the joint housing transitions from the second position to a third position as the spar is further raised above with respect to the plane of the surgical table.

8. The lift device of claim 7, wherein:
 in the first position of the joint housing, the spring device is in the compressed position and the swing arm is in the non-extended position,
 in the second position of the joint housing, the spring device is in the extended position and the swing arm is in the non-extended position, and
 in the third position of the joint housing, the spring device is in the extended position and the swing arm is in the extended position.

9. A lift device for providing lift assistance for a surgical procedure, comprising:
 a joint coupled to a surgical table and to a distal end of a spar, the spar configured to support at least one limb of a patient for the surgical procedure; and
 a spring device coupled to the joint such that the spring device is aligned with the spar, the spring device being distal to the joint relative to the spar, and the spring device configured to actuate the joint in a range between a first position and a second position, the first position corresponding to a compressed position of the spring device, the second position corresponding to an extended position of the spring device.

10. The lift device of claim 9, wherein the spring device comprises a single gas spring positioned below the spar.

11. The lift device of claim 9, wherein the joint is a ball joint.

12. The lift device of claim 9, further comprising a spring joint housing disposed between the joint and the spring device,
 wherein the spring device is configured to actuate the spring joint housing to actuate the joint.

13. The lift device of claim 12, wherein the spring joint housing is distal to the joint relative to the spar.

14. The lift device of claim 9, further comprising a swing arm coupled to the joint, the swing arm configured to actuate from a non-extended position to an extended position,
 wherein the swing arm is configured to maintain the non-extended position as the joint transitions between the first position and second position as the spar is raised with respect to a plane of the surgical table, and
 wherein the swing arm is configured to actuate from the non-extended position to the extended position when the joint transitions from the second position to a third position as the spar is further raised above with respect to the plane of the surgical table.

15. The lift device of claim 14, wherein the swing arm is coupled to the spring device via a rotational joint such that the swing arm rotates with respect to the spring device when actuated from the non-extended position to the extended position.

16. A system for providing lift assistance for a surgical procedure, comprising:
 a spar extending between a first end and a second end opposing the first end, the first end being a proximal end and the second end being a distal end, the second end coupled to a surgical table, the spar configured to be lowered and raised with respect to a plane of the surgical table; and
 a lift device, comprising:
  a joint coupled to the distal end of a spar, the spar configured to support at least one limb of a patient for the surgical procedure; and
  a spring device coupled to the joint, the spring device being distal to the joint relative to the spar and below the spar, and the spring device configured to actuate the joint in a range between a first position and a second position, the first position corresponding to a compressed position of the spring device, the second position corresponding to an extended position of the spring device.

17. The system of claim 16, wherein the spring device comprises a single gas spring, the spring device being aligned with the spar.

18. The system of claim 16, further comprising a spring joint housing disposed between the joint and the spring device,
 wherein the spring device is configured to actuate the spring joint housing to actuate the joint.

19. The system of claim 18, wherein the spring joint housing is distal to the joint relative to the spar.

20. The system of claim 18, further comprising a swing arm coupled to the joint, the swing arm being distal to the joint relative to the spar, and the swing arm configured to actuate from a non-extended position to an extended position,
 wherein the swing arm is configured to maintain the non-extended position as the joint transitions between the first position and second position as the spar is raised with respect to the plane of the surgical table, and
 wherein the swing arm is configured to actuate from the non-extended position to the extended position when the joint transitions from the second position to a third position as the spar is further raised above with respect to the plane of the surgical table.

* * * * *